(12) United States Patent
Ryan et al.

(10) Patent No.: US 8,048,152 B2
(45) Date of Patent: Nov. 1, 2011

(54) METHOD OF IMPLANTING AN ANNULOPLASTY PROSTHESIS

(75) Inventors: Timothy R. Ryan, Brooklyn Park, MN (US); Tirone E. David, Brooklyn Park, MN (US); Charles P. Tabor, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1589 days.

(21) Appl. No.: 11/411,260

(22) Filed: Apr. 26, 2006

(65) Prior Publication Data
US 2007/0078514 A1 Apr. 5, 2007

Related U.S. Application Data

(60) Provisional application No. 60/722,794, filed on Sep. 30, 2005.

(51) Int. Cl.
*A61F 2/24* (2006.01)
*A61B 17/00* (2006.01)
(52) U.S. Cl. .......... 623/2.11; 606/108; 606/206
(58) Field of Classification Search ........... 623/2.11, 623/2.36–2.42; 606/108, 148, 205, 206, 606/210; 128/898; 600/201, 220, 222, 235–240
See application file for complete search history.

(56) References Cited

U.S. PATENT DOCUMENTS

| | | | |
|---|---|---|---|
| 755,921 A | 3/1904 | O'Neill | |
| 1,452,372 A | 4/1923 | Gomez | |
| 1,974,106 A * | 9/1934 | Gardella | 606/210 |
| 3,409,013 A | 11/1968 | Berry | |
| 3,656,185 A | 4/1972 | Carpentier | |
| 3,746,002 A | 7/1973 | Haller | |
| 3,828,787 A | 8/1974 | Anderson et al. | |
| 4,042,979 A | 8/1977 | Angell | |
| 4,055,861 A | 11/1977 | Carpentier et al. | |
| 4,106,129 A | 8/1978 | Carpentier et al. | |
| 4,185,636 A | 1/1980 | Gabbay | |
| 4,204,283 A | 5/1980 | Bellhouse et al. | |
| 4,217,665 A | 8/1980 | Bex et al. | |
| 4,290,151 A | 9/1981 | Massana | |
| 4,306,319 A | 12/1981 | Kaster | |
| 4,366,581 A | 1/1983 | Shah | |
| 4,535,483 A | 8/1985 | Klawitter | |

(Continued)

FOREIGN PATENT DOCUMENTS

GB 2083362 2/1982

(Continued)

OTHER PUBLICATIONS

Surgical Techniques for the Repair of Anterior Mitral Leaflet Prolapse / Carlos M.G. Duran, M.D., Ph.D./ J Card Surg 1999; 14:471-481.

(Continued)

*Primary Examiner* — Julian Woo
*Assistant Examiner* — Christopher L Templeton

(57) ABSTRACT

A simplified and more easily employed tool for holding an implantable annuloplasty prosthesis during passage of sutures through the prosthesis and for conveniently and efficiently releasing the prosthesis from the tool. Separation of the implantable prosthesis and the tool may be conveniently accomplished without requiring the use of a sharp instrument. Attachment between the prosthesis and its surgical carrying tool can be accomplished in a suture-less fashion. The tool includes a suture management device in some embodiments for selectively receiving and maintaining sutures otherwise securing the prosthesis to tissue.

13 Claims, 15 Drawing Sheets

U.S. PATENT DOCUMENTS

| | | | |
|---|---|---|---|
| 4,612,011 A | 9/1986 | Kaultzky | |
| 4,648,401 A | 3/1987 | Mattson | |
| 4,655,218 A | 4/1987 | Kulik et al. | |
| 4,702,250 A | 10/1987 | Ovil et al. | |
| 4,743,253 A | 5/1988 | Magladry | |
| 4,755,181 A | 7/1988 | Igoe | |
| 4,865,600 A | 9/1989 | Carpentier et al. | |
| 4,911,164 A | 3/1990 | Roth | |
| 4,932,965 A | 6/1990 | Phillips | |
| 5,011,481 A | 4/1991 | Myers et al. | |
| 5,041,130 A | 8/1991 | Cosgrove et al. | |
| 5,059,198 A | 10/1991 | Gimpelson | |
| 5,059,214 A | 10/1991 | Akopov et al. | |
| 5,071,428 A | 12/1991 | Chin et al. | |
| 5,104,407 A | 4/1992 | Lam et al. | |
| 5,197,979 A | 3/1993 | Quintero et al. | |
| 5,201,739 A | 4/1993 | Semm | |
| 5,211,655 A | 5/1993 | Hasson | |
| 5,217,460 A | 6/1993 | Knoepfler | |
| 5,241,968 A | 9/1993 | Slater | |
| 5,290,300 A | 3/1994 | Cosgrove et al. | |
| 5,306,296 A | 4/1994 | Wright et al. | |
| 5,318,040 A | 6/1994 | Kensey et al. | |
| 5,338,317 A * | 8/1994 | Hasson et al. | 606/206 |
| 5,350,420 A | 9/1994 | Cosgrove et al. | |
| 5,383,886 A | 1/1995 | Kensey et al. | |
| 5,415,667 A | 5/1995 | Frater | |
| 5,431,675 A * | 7/1995 | Nicholas et al. | 606/170 |
| 5,496,336 A | 3/1996 | Cosgrove et al. | |
| 5,522,884 A | 6/1996 | Wright | |
| 5,638,402 A | 6/1997 | Osaka et al. | |
| 5,713,951 A * | 2/1998 | Garrison et al. | 128/898 |
| 5,752,972 A | 5/1998 | Hoogeboom | |
| 5,906,642 A | 5/1999 | Caudillo et al. | |
| 5,984,959 A | 11/1999 | Robertson et al. | |
| 6,159,240 A | 12/2000 | Sparer et al. | |
| 6,174,332 B1 | 1/2001 | Loch et al. | |
| 6,183,512 B1 | 2/2001 | Howanec, Jr. et al. | |
| 6,283,993 B1 | 9/2001 | Cosgrove et al. | |
| 6,319,280 B1 | 11/2001 | Schoon | |
| 6,332,893 B1 | 12/2001 | Mortier et al. | |
| 6,406,492 B1 | 6/2002 | Lytle | |
| 6,409,758 B2 | 6/2002 | Stobie et al. | |
| 6,451,054 B1 * | 9/2002 | Stevens | 623/2.11 |
| 6,558,416 B2 | 5/2003 | Cosgrove et al. | |
| 6,702,852 B2 | 3/2004 | Stobie et al. | |
| 6,719,786 B2 | 4/2004 | Ryan et al. | |
| 6,786,924 B2 | 9/2004 | Ryan et al. | |
| 6,955,689 B2 | 10/2005 | Ryan et al. | |
| 2001/0049558 A1 | 12/2001 | Liddicoat et al. | |
| 2002/0002385 A1 * | 1/2002 | Boche et al. | 606/205 |
| 2002/0129820 A1 | 9/2002 | Ryan et al. | |
| 2003/0176917 A1 | 9/2003 | Ryan et al. | |
| 2004/0006384 A1 | 1/2004 | McCarthy | |
| 2004/0019357 A1 | 1/2004 | Campbell et al. | |
| 2004/0024451 A1 | 2/2004 | Johnson et al. | |
| 2004/0034410 A1 * | 2/2004 | Holmberg | 623/2.11 |
| 2004/0210305 A1 | 10/2004 | Shu et al. | |
| 2005/0065597 A1 | 3/2005 | Lansae | |
| 2005/0125015 A1 | 6/2005 | McNally-Heintzelman et al. | |
| 2005/0197696 A1 | 9/2005 | Duran | |

FOREIGN PATENT DOCUMENTS

| | | |
|---|---|---|
| GB | 2108393 | 5/1983 |
| SU | 878285 | 11/1981 |
| WO | WO 00/59408 | 10/2000 |
| WO | 2004/041099 | 5/2004 |
| WO | 2005/055883 | 6/2005 |

OTHER PUBLICATIONS

Medtronic Booklet "Medtronic Duran Flexible Annuloplasty Systems In-Service Guide" / UC200004685 EN.

Carpentier-Edwards Physio Annuloplasty Ring, "Technical Product Manual," Baxter (1996) (22 pages).

Ian J. Reece, M.B., F.R.C.S., et al., "Surgical Treatment of Mitral Systolic Click Syndrome: Results in 37 Patients," The Annuals of Thoracic Surgery, vol. 39, No. 2, Feb. 1985 (pp. 155-158).

Denton A. Cooley, M.D., et al., "Mitral Leaflet Prolapse: Surgical Treatment using a Posterior Annular Collar Prosthesis," Cardiovascular Diseases, Bulletin of the Texas Heart Institute, vol. 3, Nov. 4, 1976 (pp. 438-439; 442-443).

Ormiston, et al., "Size and Motion in the Mitral Valve Annulus in Man," Circulation (1981) 64:113.

Dagum, et al., "Potential Mechanism of Left Ventricular Outflow Tract Obstruction After Mitral Ring Annuloplasty," J. Thorac. Cardiovasc. Surg. (1999) 117:472-80.

David, et al., "Left Ventricular Function After Mitral Valve Surgery," J. Heart Dis. (1995) 4:S175-80.

Duran, "Perspectives for Acquired Valvular Disease," Advanced Cardiac Surgery (1993) vol. 4.

Okada, et al., "Comparison of the Carpentier and Duran Prosthetic Rings Used in Mitral Reconstruction," Ann. Thorac. Surg. (1995) 59:658-63.

Duran, et al., "Clinical and Hemodynamic Performance of a Totally Flexible Prosthetic Ring for Atrio-Ventricular Valve Reconstruction," Ann. Thorac. Surg. (1976) 22:458-63.

Van Rijk-zwikker, et al., "Comparison to Flexible Rings for Annuloplasty of the Mitral Valve," Circulation (1990) 82 (Suppl. IV):IV 58-64.

U.S. Appl. No. 11/411,273's NFOA (mailed Oct. 14, 2009); 11 pgs.

\* cited by examiner

METHOD OF IMPLANTING AN ANNULOPLASTY PROSTHESIS

CROSS-REFERENCE TO RELATED APPLICATIONS

This application claims the benefit under §119(e)(1), and incorporates herein by reference an entirety of, U.S. Provisional Application No. 60/722,794, filed Sep. 30, 2005 and entitled "Method of Implanting an Annuloplasty Prosthesis."

BACKGROUND OF THE INVENTION

The present invention relates generally to surgical tools and methods of implantation. More particularly, it relates to surgical tools and methods used in conjunction with heart repair procedures, including tools for holding prostheses such as annuloplasty rings or bands.

Improvements in cardiopulmonary bypass and myocardial protection and standardization of surgical techniques have lead to increasing interest in valve reconstruction procedures. See, for example, Ormiston J A, Shah P M, Tei C, et al., Size and Motion in the Mitral Valve Annulus in Man, *Circulation* 1981;64:113; Dagum P, Green GR, Glasson J R, et al., Potential Mechanism of Left Ventricular Outflow Tract Obstruction After Mitral Ring Annuloplasty, *J Thorac Cardiovasc Surg.* 1999;117:472-80; David T E, Armstrong S, Sun Z, Left Ventricular Function After Mitral Valve Surgery, *J Heart Dis* 1995; 4:S175-80; and Duran C, Perspectives for Acquired Valvular Disease, *Advanced Cardiac Surgery*, Vol. 4, 1993.

As highlighted by the above, annuloplasty bands and rings have been recognized as being highly useful in a variety of surgical procedures, including mitral and tricuspid valve repair. In general terms, current techniques for implanting an annuloplasty ring or band includes the annuloplasty device initially being secured to a holder that facilitates simplified manipulation of the annuloplasty device during the implantation procedure. Because heart valve annulus size varies from patient to patient, a plurality of sizers are typically used to identify the appropriate size for the holder. Once the appropriate size is identified, the correspondingly-sized holder is selected from an inventory of different sized holders. This process can be time consuming and requires large inventories of both sizers and holders.

Once the appropriately-sized holder/annuloplasty device has been selected, sutures are then placed around all or portions of the valve annulus at spaced intervals. To this end, a typical suture arrangement entails looping a suture through the annular tissue that opposing ends or segments of the suture define a suture pair. With this technique, a plurality of sutures are employed, thus defining a plurality of suture pairs (i.e., once looped through the annular tissue, opposing ends or segments of the suture extend from the annular tissue to define a "suture pair"). Spacing along the annular tissue between the segments associated with a particular suture pair can vary depending upon whether it is desired to plicate (or reduce) a region of the annulus to which the suture pair is applied (e.g., a suture pair will be spaced approximately 4 mm in width where no plication is necessary, and approximately 5-6 mm in width where plication is desired). Regardless, the sutures are then brought through the annuloplasty device (with an equal spacing between suture pair segments relative to the annuloplasty device determined by whether or not plication is desired).

The process of passing the sutures through the annuloplasty device occurs while the prosthesis is maintained by the holder/tool at a point spaced from the valve annulus. For virtually all procedures in which multiple sutures, and thus multiple suture segment pairs, are required, once threaded through the annuloplasty device, the suture segments must be discretely positioned and held away from the surgical site so as to not interfere with threading of other suture segments through the annuloplasty device, to avoid entanglement with other suture segments, maintain an organizational flow to the threading of sutures, etc. The conventional approach to this suture management requirement entails securing the sutures within one or more separate suture holding devices located away from the surgical field. Unfortunately, the sutures can become entangled and it is sometimes difficult to identify corresponding segments of a suture pair.

Once all necessary suture segments have been placed through the annuloplasty device, the annuloplasty device is then removed from the holder. Conventional annuloplasty holders entail the use of one or more sutures that secure the annuloplasty device to the holder. With this approach, to release the annuloplasty device, a sharp instrument such as a knife or scalpel is used to cut the suture(s) that otherwise connects the annuloplasty device to the holder frame. While accepted, this has the disadvantage of requiring the use of a sharp instrument in close proximity to sensitive anatomical structures and in even closer proximity to the prosthetic repair device which typically has a fabric cover that can otherwise be relatively easily severed. Further, known annuloplasty device holder designs give rise to the potential of improperly separating the device-retaining suture(s) in more than one location. This may increase the chance that a stray piece of the cut suture(s) may remain in the patient's body.

Various systems for use in heart repair procedures are disclosed in U.S. Pat. Nos. 5,011,481; 5,290,300; 5,496,336; 5,638,402; 5,522,884; 6,174,332; 6,283,993; 6,558,416; and 6,719,786. Prosthesis and surgical methods for implanting prostheses for addressing heart disorders are described in Okada Y, Shomura T, Yamura Yl, et al., Comparison of the Carpentier and Duran Prosthetic Rings Used in Mitral Reconstruction, *Ann Thorac Surg* 1995; 59:658-63; Duran C M G; Ubago J L M; Clinical and Hemodynamic Performance of a Totally Flexible Prosthetic Ring for Atrio-Ventricular Valve Reconstruction, *Ann Thorac Surg* 1976; 22:458-63; and Van Rijk-zwikker GL, Mast F, Shepperheyn J J, et al., Comparison to Flexible Rings for Annuloplasty of the Mitral Valve, *Circulation*, 1990; 82 (Suppl. IV):IV 58-64.

Annuloplasty devices continue to be highly important tools for repairing heart valves. Unfortunately, the instruments used in connection with implantation of the annuloplasty prosthesis are cumbersome. Therefore, a need exists for an implantation tool and related surgical method for implanting an annuloplasty device.

SUMMARY

In one aspect, the present invention generally is directed toward a simplified and more easily employed tool for holding an implantable annuloplasty prosthesis during passage of sutures through the prosthesis and for conveniently and efficiently releasing the prosthesis from the tool. Separation of the implantable prosthesis and the tool may be conveniently accomplished without requiring the use of a sharp instrument. Attachment between the prosthesis and the surgical carrying tool can be accomplished in a suture-less fashion.

In one embodiment, a tool for use in implanting an annuloplasty prosthesis to repair a heart valve is provided and includes an elongate proximal portion and a distal portion. The proximal portion forms a handle. The distal portion includes first and second jaws, at least one of which is mounted for relative movement between an open state and a closed state. In the open state, an end section of the first jaw is spaced apart from a corresponding end section of the second jaw. In the closed state, a spacing between the corresponding end sections of the jaws is less than the spacing in the open state. In one preferred embodiment, the tool further includes an actuator mechanism having an exteriorly accessible actuator providing a single actuation point for a user to effectuate transition of the jaws from the closed state to the open state in releasing an annuloplasty prosthesis from the tool. In another preferred embodiment, the tool further includes a suture management device.

In another aspect, the present invention generally is directed toward a method of repairing a heart valve by implanting an annuloplasty prosthesis. The method is characterized by the absence of a need to employ a sharp instrument to effectuate release of the annuloplasty device from a tool otherwise maintaining the annuloplasty device during a portion of the implantation procedure.

In one embodiment, the method includes providing an implantable annuloplasty prosthesis and a tool. The tool has first and second jaws, at least one of which is movable relative to the other between an open state and a closed state. In the open state, an end section of the first jaw is spaced apart from a corresponding end section of the second jaw. In the closed state, a spacing between the corresponding end sections is less than the spacing in the open state. With this in mind, the jaws are transitioned to the open state, and the implantable prosthesis is positioned against the end section of at least one of the jaws. The implantable prosthesis is secured to the tool by transitioning the jaws to the closed state. At least one suture is attached to heart tissue and then passed through the implantable prosthesis while the implantable prosthesis is otherwise secured to the tool. The jaws are transitioned to the open state and the implantable prosthesis is removed from the tool. Once removed, the implantable prosthesis is moved to an implant location and at least one suture is secured so that it resists movement of the implantable prosthesis relative to the heart tissue. In one preferred embodiment, segments of at least one suture are selectively maintained by a suture management device provided by the tool.

DETAILED DESCRIPTION

Tool 20

Figure 1A:
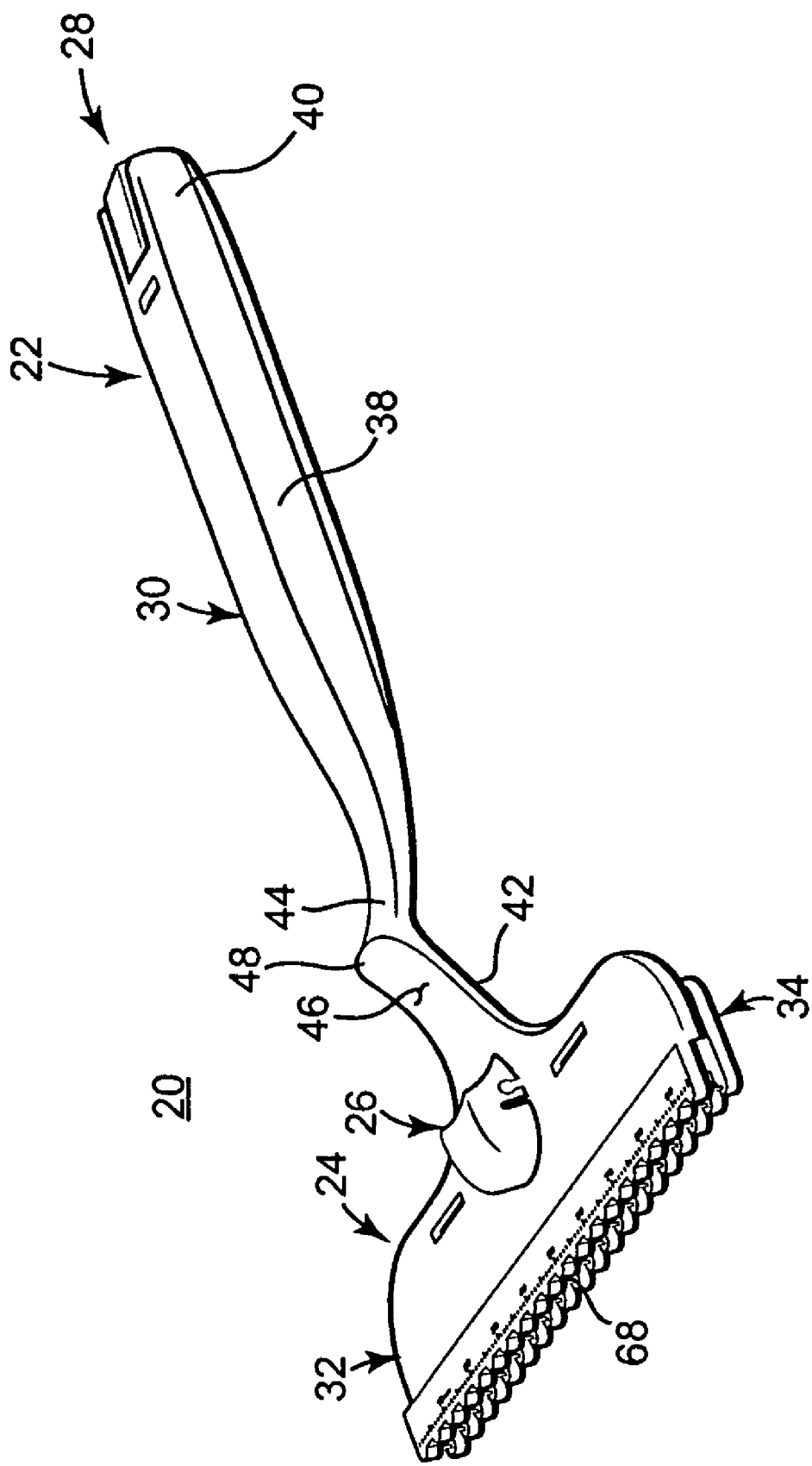
FIG. 1A is a perspective view of one embodiment of a tool for use in implanting an annuloplasty prosthesis according to principles of the present invention.
Figure 1B:
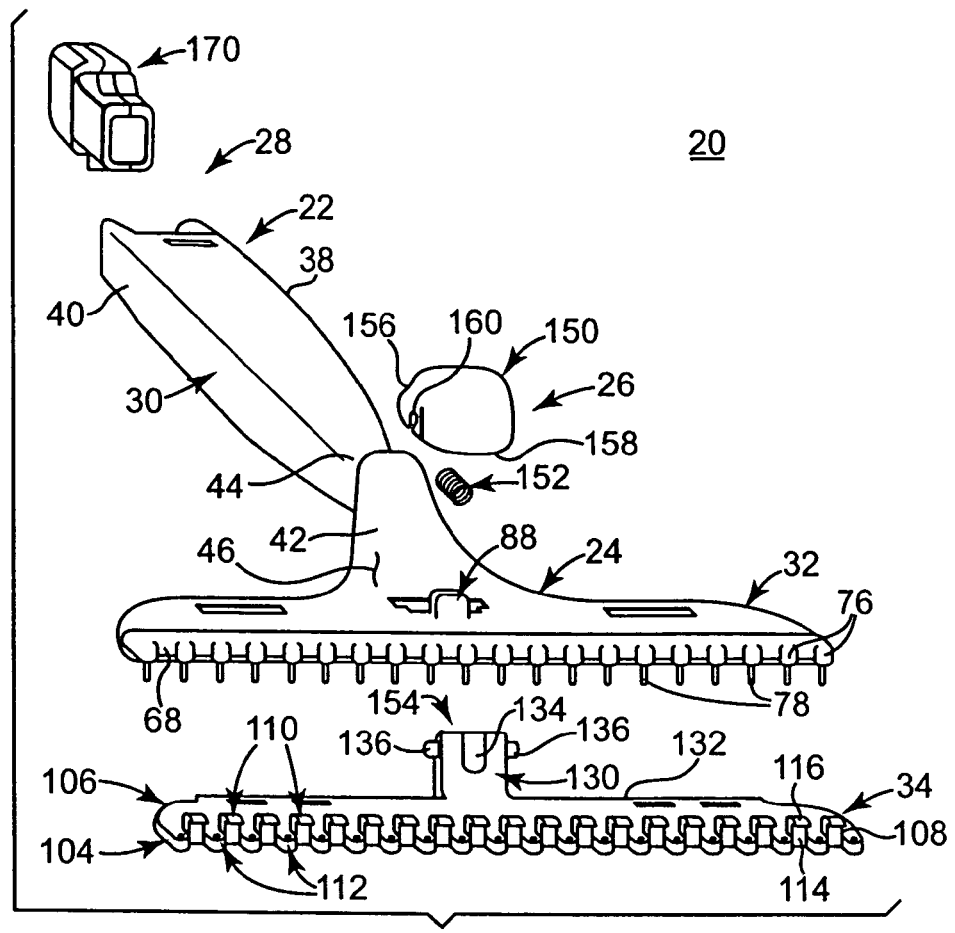
FIG. 1B is an exploded view of the tool of FIG. 1A.

One embodiment of a tool 20 for use in implanting an annuloplasty prosthesis (not shown) such as an annuloplasty band or ring is shown in FIGS. 1A and 1B. The tool 20 includes an elongate proximal portion 22, a distal portion 24, an actuator mechanism 26 (referenced generally), and a suture management device 28. Details on the various components are provided below. In general terms, however, the proximal portion 22 defines a handle 30 that is sized and shaped to be manually grasped by a single hand of a user. The distal portion 24 includes first and second jaws 32, 34 mounted for relative movement between i) an open state in which the jaws 32, 34 are spaced apart to receive or release an implantable annuloplasty prosthetic, and ii) a closed state (shown in FIG. 1A) in which the first and second jaws 32, 34 are spaced closer together than in the open state. The actuator mechanism 26 facilitates movement of the jaws 32, 34 between the open and closed states. With this construction, the tool 20 facilitates annuloplasty device implantation without requiring a cutting instrument to effectuate release of the annuloplasty device from the tool 20. Finally, the suture management device 28 provides a convenient system for selectively maintaining one or more sutures (not shown) on the tool 20 itself.

The proximal portion 22 defines the handle 30 to generally have an intermediate segment 38 extending between a proximal end 40 and a distal neck 42. In one embodiment, and as described in greater detail below, the proximal end 40 forms a portion of the suture management device 28. Regardless, the neck 42 extends from the intermediate segment 38 to define a transition of the proximal portion 22 to the distal portion 24. In one embodiment, the intermediate segment 38 defines a curvature 44 adjacent the neck 42, with the curvature 44 providing an ergonomically convenient location for a user's thumb (not shown) during normal handling of the tool 20. In addition, an upper surface 46 of the neck 42 extends downwardly (relative to a central axis of the handle 30) from the intermediate segment 38 in a curved fashion. With this configuration, a user's thumb readily engages a component of the actuator mechanism 26 as the handle 30 is otherwise grasped in the user's palm, as described in greater detail below. To this end, the neck 42 defines a ledge 48 relative to the intermediate segment 38. The ledge 48 is sized and shaped to provide a perceptible stop surface for the user's thumb to impede accidental user activation of the actuator mechanism 26 during normal handling of the tool 20. Alternatively, the handle 30, including the neck 42, can assume a wide variety of other shapes, sizes, or configurations.

First Jaw 32

The distal portion 24 extends from the neck 42 and, as previously described, includes the first jaw 32 and the second jaw 34. With additional reference to FIGS. 2A and 2B, in one embodiment, the first jaw 32 includes an upper surface 60 and a lower surface 62, and defines an end section 64 and a base section 66. In one embodiment, the first jaw 32 is homogenously and integrally formed with the neck 42 such that the upper surfaces 46, 60 are continuous. Alternatively, the first jaw 32 can be formed separately.

The end section 64 terminates at a leading end 68. The leading end 68 defines an elongated surface corresponding with a portion of the second jaw 34 for assisting in retaining an annuloplasty prosthesis (not shown) relative to the second jaw 34 as described below. In this regard, the leading end 68 is substantially linear and elongated, defining a plane that is substantially perpendicular to a longitudinal axis of the handle 30 (best shown in FIGS. 1A and 1B). Stated otherwise, a width defined by the leading end 68 (i.e., dimension transverse to an axis of the handle 30) is greater than a width of the neck 42.

Figure 2A:
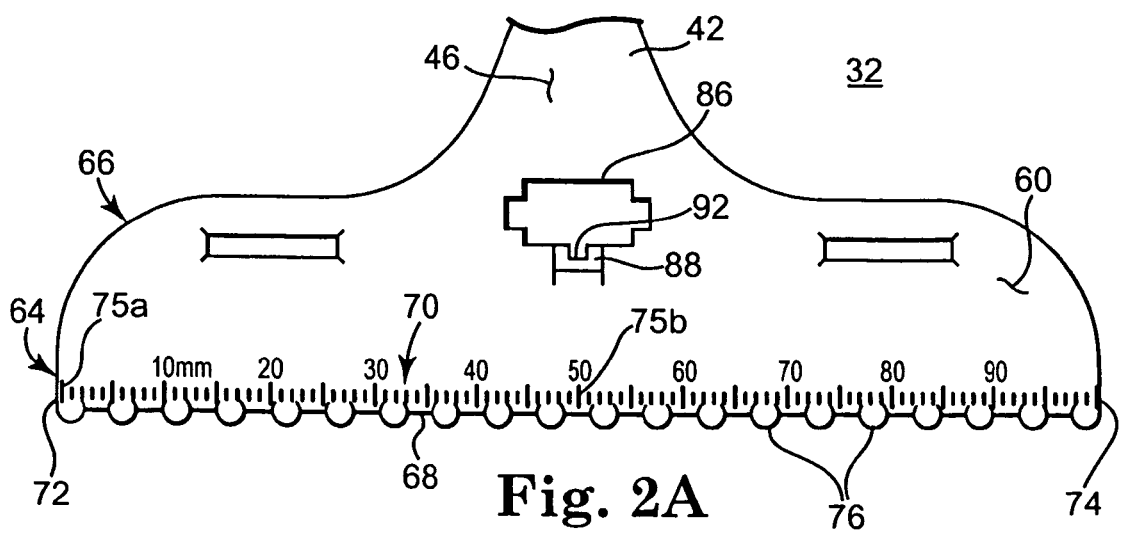
FIG. 2A is a top plan view of a first jaw portion of the tool of FIG. 1A.

In one embodiment, and as best shown in FIG. 2A, the upper surface 60 at the end section 64 includes indicia 70 (referenced generally) representing incremental units of measurement (e.g., millimeters) extending from a first side 72 of the end section 64 to a second side 74. For example, a first mark 75a adjacent the first side 72 is indicative of a "zero" point, with additional markings representing measured distances from the zero mark 75a (e.g., a second mark 75b in FIG. 2A is 50 mm from the zero mark 75a). As described in greater detail below, the indicia 70 facilitates accurate placement of sutures (not shown) through an annuloplasty prosthetic otherwise secured to the tool 20, as well as an indication of a length of the prosthetic. In addition, or as an alternative to the "dash" marks, the indicia 70 can include other nomenclature such as numbers, words, (e.g., that explain use of the tool 20), symbols, etc. In alternative embodiments, the indicia 70 is omitted.

Figure 2B:
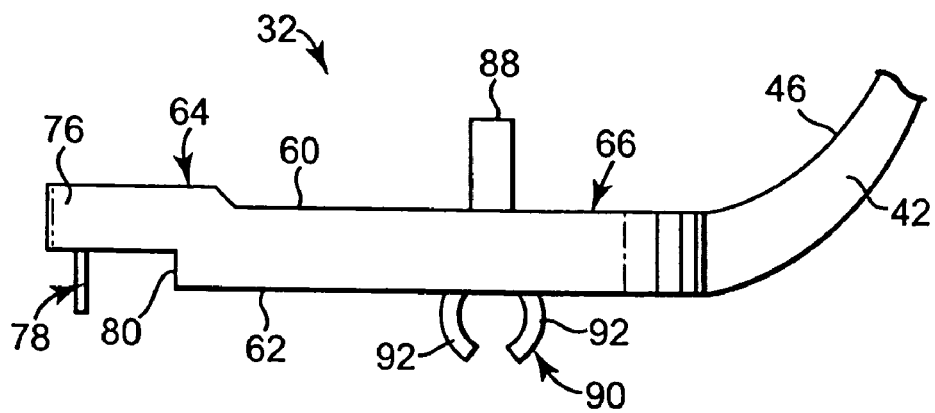
FIG. 2B is a side view of the first jaw of FIG. 2A.

Finally, in one embodiment, the end section 64 includes a plurality of protrusions 76 extending distally from the leading end 68. As best shown in FIGS. 1B and 2B, each of the protrusions 76 maintains a holding member 78. The holding members 78 project downwardly relative to the lower surface 62 (as best shown in FIG. 2B) and are adapted to penetrate into an annuloplasty prosthesis (not shown) otherwise maintained by the second jaw 34, to resist separation between the annuloplasty device and the tool 20 as described in greater detail below. The protrusions 76, and thus the holding members 78, are uniformly spaced along a width of the end section 64 in one embodiment; alternatively, the holding members 78 can be non-uniformly spaced. In one embodiment, the holding members 78 are uniformly sized pins, but can assume a variety of other acceptable forms such as ribs, detents, barbs, pegs, needles, etc., that do not necessarily have to "enter" the annuloplasty prosthesis in order to retain the prosthesis relative to the tool 20. Regardless, in one embodiment and as best shown in FIG. 2B, the end section 64 defines a step 80 (relative to the base section 66) along the lower surface 62 to accommodate a length of the holding members 78 as well as a corresponding feature of the second jaw 34 as described below.

The base section 66 extends from the neck 42 to the end section 64 and, in one embodiment, forms an opening 86 and includes a post 88 and mounting elements 90. The opening 86 extends through a thickness of the base section 66 adjacent the opening 86 and is sized to receive a portion of the actuator mechanism 26 (FIG. 1B), as described in greater detail below.

Along these same lines, the upper surface 60 along the base section 66 is preferably flat to facilitate operation of the actuator mechanism 26. Similarly, the post 88 forms a component of the actuator mechanism 26, and is described in greater detail below. In general terms, however, the post 88 extends upwardly from the upper surface 60 adjacent the opening 86 and forms a channel 92.

Figure 2C:
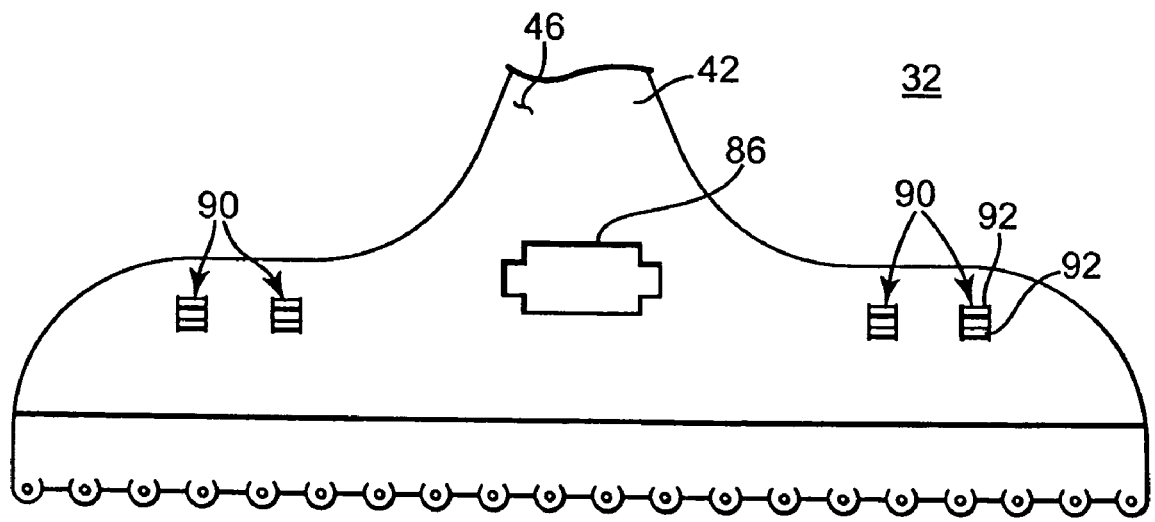
FIG. 2C is a bottom plan view of the first jaw of FIG. 2A.

With reference to FIGS. 2B and 2C, the mounting elements 90 are formed on or extend from the lower surface 62, and are adapted to facilitate mounting of the first and second jaws 32, 34 to one another in a manner that allows hinged or pivoting movement of the jaws 32, 34. In one embodiment, the mounting elements 90 are pairs of opposing clamp fingers 92. While four of the clamp fingers 92 are shown (FIG. 2C), any other number, either greater or lesser, is also acceptable. Alternatively, a wide variety of pivotable mounting configurations can be employed.

Second Jaw 34

Figure 3A:
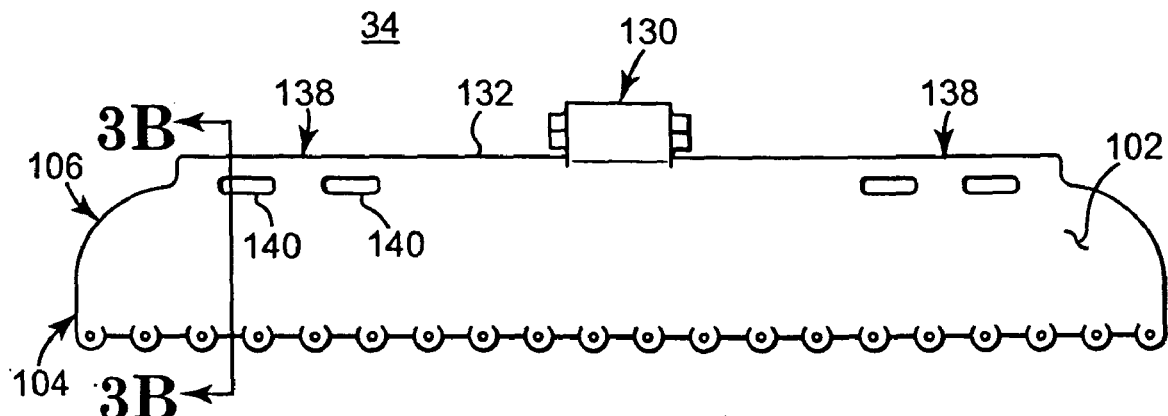
FIG. 3A is a bottom plan view of a second jaw portion of the tool of FIG. 1A.
Figure 3B:
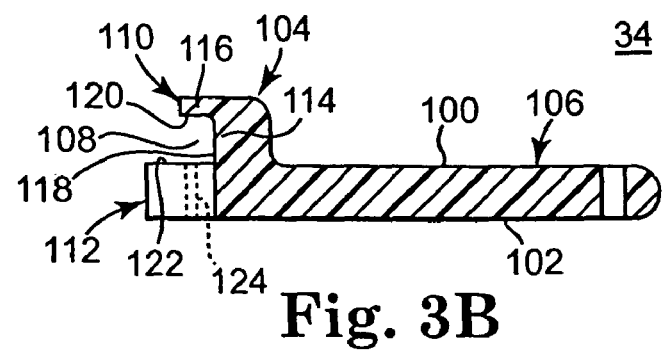
FIG. 3B is a cross-sectional view of the second jaw of FIG. 3A.

Returning to FIG. 1B, and with additional reference to FIGS. 3A and 3B, the second jaw 34 includes an inner surface 100 (FIG. 3B) and an outer surface 102, and defines an end section 104 and a base section 106. The end section 104 defines a channel 108 (best shown in FIGS. 1B and 3B) sized to receive an annuloplasty prosthesis (not shown). In this regard, the channel 108 is defined, in one embodiment, by a plurality of fingers 110 and a plurality of projections 112. Each of the fingers 110 includes a base 114 and a head 116. As best shown in FIG. 3B, the base 114 extends upwardly from the inner surface 100, with the collective bases 114 combining to define a lateral face 118 of the channel 108. The head 116 extends distally from the base 114 opposite the inner surface 100, with the collective heads 116 combining to define a first longitudinal face 120 of the channel 108. The plurality of fingers 110 are intermittently spaced so as to accommodate passage of the holding members 78 (FIG. 1B) associated with the first jaw 32.

The projections 112 extend substantially parallel to the first longitudinal face 120 provided by the heads 116, and combine to define a second longitudinal face 122 of the channel 108. In one embodiment, the projections 112 are intermittently spaced. Alternatively, however, a continuous structure can be defined. In one embodiment, each of the projections 112 forms a hole 124 sized to receive a corresponding one of the holding members 78. Alternatively, depending upon the exact configuration of the holding member 78, the projections 112 can assume a variety of other forms. Regardless, the lateral face 118, the first longitudinal face 120, and the second longitudinal face 122 each serve as a receiving surface against which an annuloplasty prosthesis (not shown) can be placed. Thus, the channel 108 serves as a holding zone for the annuloplasty prosthesis as described below. As shown in FIG. 1B, the channel 108 is substantially linear, extending in a plane substantially perpendicular to an axis of the handle 30.

In one embodiment and with specific reference to FIG. 1B, the base section 106 includes a post 130 extending from a trailing edge 132 thereof. The post 130 forms a portion of the actuator mechanism 26. In general terms, however, the post 130 extends in a generally perpendicular fashion relative to the end section 104 and forms a slot 134. In addition, the post 130 includes opposed tabs 136 extending in a transverse fashion. The slot 134 and the tabs 136 facilitate assembly of the actuator mechanism 26, with the post 130 adapted to translate a force onto the end section 104. In addition, and as best shown in FIG. 3A, the base section 106 of the second jaw 34 forms engagement segments 138 adapted to facilitate mounting of the second jaw 34 to the first jaw 32 (FIG. 1B). For example, in one embodiment, the engagement segments 138 are defined by one or more apertures 140 formed adjacent the trailing edge 132. The apertures 140 are sized to receive a respective one of the clamp fingers 92 (FIG. 2B), with the trailing edge 132 at each of the engagement segments 138 serving as a pivot point for movement of the second jaw 34 relative to the first jaw 32.

Actuator Mechanism 26

The actuator mechanism 26 includes, in one embodiment, an actuator 150, a biasing device 152, and a capturing assembly 154 (referenced generally in FIG. 1B), that, in one embodiment, includes the post 88 associated with the first jaw 32 and the post 130 associated with the second jaw 34. In general terms, the actuator 150 provides a force-receiving surface for a user to effectuate movement of the jaws 32, 34, with the biasing device 152 forcing the actuator mechanism 26 to a naturally closed state.

The actuator 150 can assume a variety of forms, but in one embodiment is a button defining a pressing surface 156 (referenced generally in FIG. 1B) and a guide surface 158. The pressing surface 156 is preferably contoured to readily receive a single digit (i.e., thumb or finger) of a user. The guide surface 158 is preferably smooth for reasons described below. In one embodiment, the actuator 150 is formed as a shell, defining an interior region within which various other components of the actuator mechanism 26 can reside. Further, the actuator 150 is configured for attachment to the post 130 provided by the second jaw 34 via opposing notches 160 (one of which is shown in FIG. 1B) that otherwise engage a respective one of the tabs 136. Alternatively, a variety of other configurations can be employed to accomplish assembly of the actuator 150 to the post 130. Preferably, however, the actuator 150 can slightly pivot relative to the post 130 (e.g., in one embodiment, the notches 160 are sized to allow pivoting of the actuator 150 relative to the tabs 136).

The biasing device 152 is, in one embodiment, a compression spring adapted to bias the posts 88, 130 away from one another, as described below. With this configuration, then, the spring 152 biases the end sections 64, 104 of the jaws 32, 34 to the closed state of FIG. 1A. Alternatively, the biasing device 152 can assume a variety of other forms. Even further, in other embodiments, the biasing device 152 is eliminated. More particularly, the actuator mechanism 26 can be configured to include or define structures associated with the first and second jaws 32, 34 that serve to selectively lock the jaws 32, 34 in the closed state. As described below, an annuloplasty prosthesis (not shown) is secured by the jaws 32, 34 in the closed state, such that by facilitating "locking" of the jaws 32, 34 in the closed state, unintended dislodgement of the prosthesis from the jaws 32, 34 is prevented. For example, a detent assembly can be provided (e.g., the post 130 forms a protrusion sized to be captured within a corresponding aperture formed along the opening 86 when the jaws 32, 34 are in the closed state) that effectively serves the same function as the biasing device 152.

Jaw/Actuator Mechanism Assembly

Figure 4A:
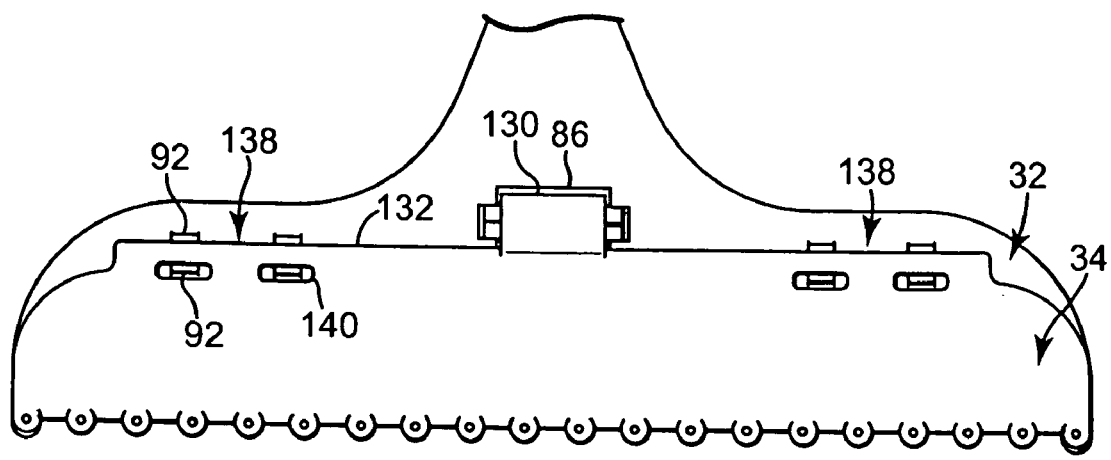
FIG. 4A is a bottom plan view of a distal portion of the tool of FIG. 1A illustrating assembly of an actuator mechanism.
Figure 4B:
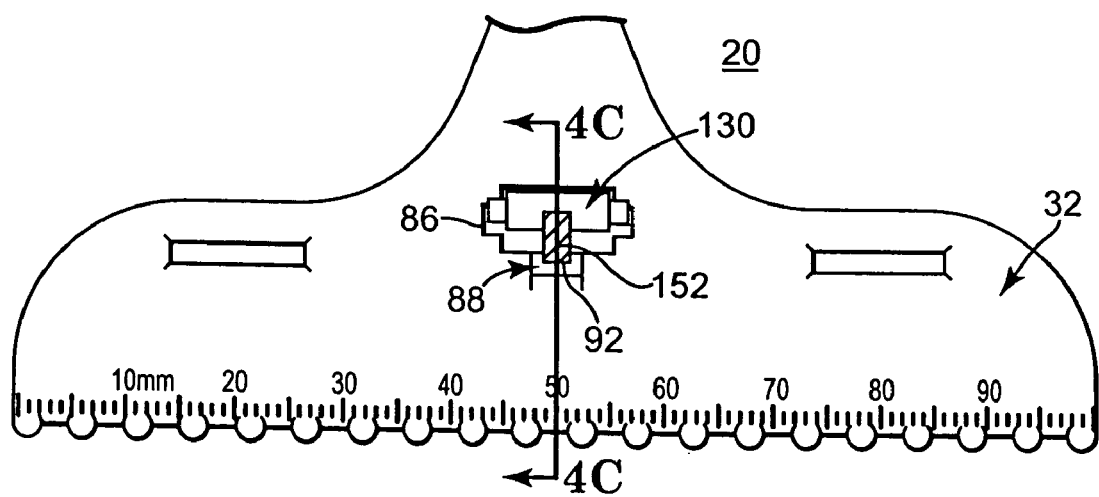
FIG. 4B is a top plan view of the distal portion of FIG. 4A.

Assembly of the actuator mechanism 26, the first jaw 32, and the second jaw 34 is best described with reference to FIGS. 4A-4C. The second jaw 34 is pivotally mounted to the first jaw 32 by inserting the engagement segments 138 of the second jaw 34 within the clamping fingers 92 of the first jaw 32 as best shown in FIG. 4A. In particular, each of the respective pairs of clamping fingers 92 capture the corresponding engagement segment 138 via the trailing edge 132 and the apertures 140. With this assembly, then, the second jaw 34 can pivot relative to the first jaw 32 via rotation of the end segments 138 within the mounting elements 90, respectively. In addition, and as best shown in FIG. 4B (that otherwise illustrates the tool 20 with the actuator 150 removed), the post 130 of the second jaw 34 protrudes through the opening 86 in the first jaw 32. The biasing device 152 is captured at opposing ends thereof within the posts 88, 130. More particularly, the biasing device 152 nests within the channel 92 of the post 88 and the slot 134 of the post 130. Finally, as shown in FIG. 4C, the actuator 150 is assembled to the post 130 of the second jaw 34, for example by placing the actuator 150 over the post 130 such that the tabs 136 (FIG. 1B) are received within respective ones of the notches 160 (FIG. 1B).

Figure 4C:
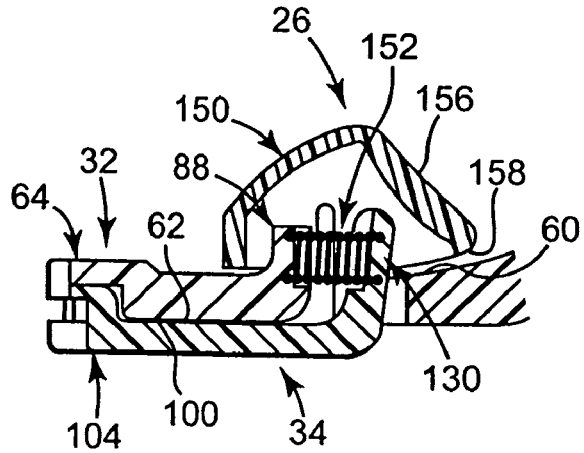
FIG. 4C is a cross-sectional view of the tool of FIG. 4B taken along the lines 4C-4C.

The final assembly is shown in FIG. 4C. Once assembled, the biasing device 152 forces the jaws 32, 34 to a closed state as shown (i.e., forces or biases the post 130 of the second jaw 34 away from the post 88 of the first jaw 32). In particular, a force imparted on the post 130 by the biasing device 152 is translated along the second jaw 34 to the connection point between the jaws 32, 34 (i.e., interface between the mounting elements 90/end segments 138 as shown in FIG. 4A), thus forcing the end sections 64, 104 toward one another, with the lower surface 62 of the first jaw 32 abutting the inner surface 100 of the second jaw 34. Alternatively, the actuator mechanism 26, the first jaw 32, and/or the second jaw 34 can assume a variety of other forms capable of effectuating a biased, closed state and selective movement to an open state.

Figure 5:
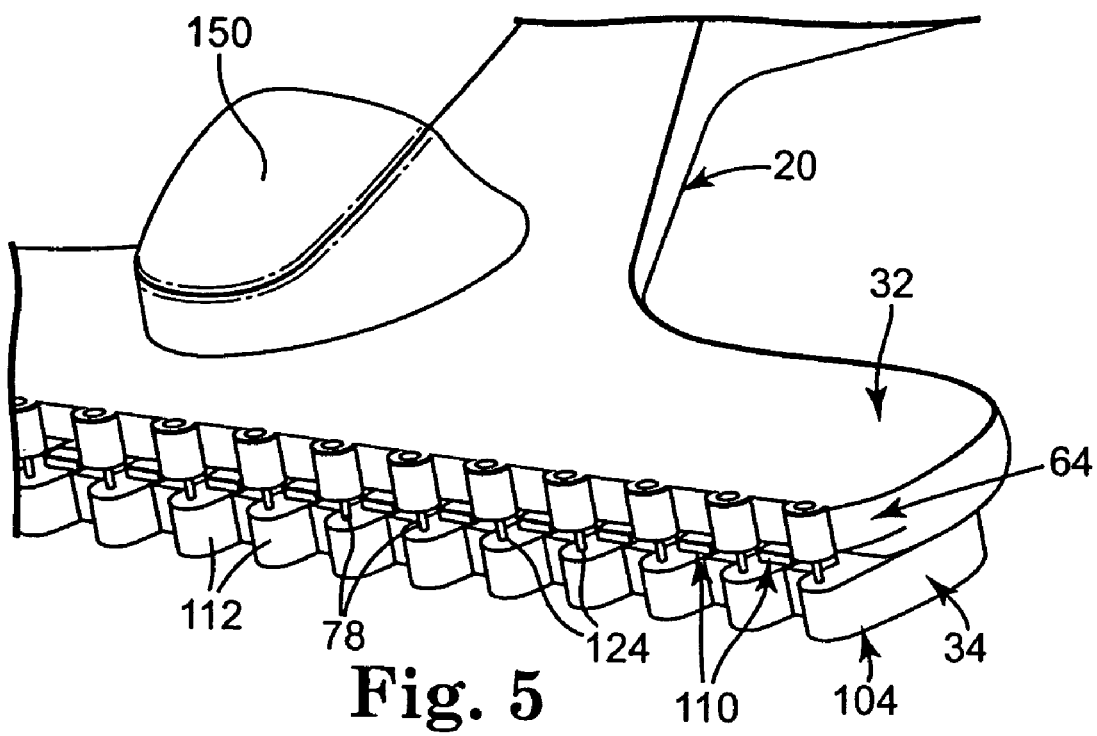
FIG. 5 is a perspective view of a portion of the tool of FIG. 1A showing the jaws in a closed state.

A closed state of the jaws 32, 34 is better illustrated in FIG. 5. In particular, the end sections 64, 104 are in close proximity to one another, with the holding members 78 received within respective ones of the holes 124 (shown generally) provided by the projections 112 of the second jaw 34. A spacing and arrangement of the holding members 78 corresponds with that of the fingers 110, such that respective ones of the holding members 78 are positioned between adjacent fingers 110 and vice-versa.

Figure 6:
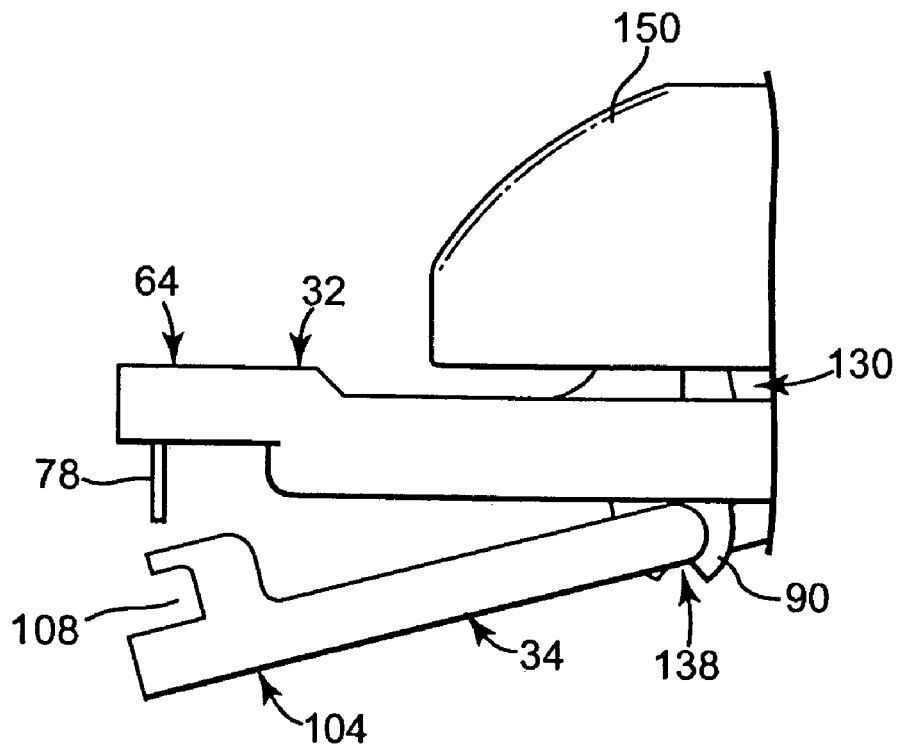
FIG. 6 is a side view of the portion of the tool of FIG. 1A showing the jaws in an open state.

The jaws 32, 34 can be transitioned to an open state via the actuator mechanism 26 and in particular via a force applied to the actuator 150. With reference to FIG. 4C, a user-applied force is imparted upon the pressing surface 156 of the actuator 150 and is thus translated to the post 130 of the second jaw 34. When the user-applied force is sufficient to overcome a bias of the biasing device 152, the post 130 of the second jaw 34 moves toward the post 88 of the first jaw 32, with the actuator 150 sliding relative to the first jaw 32 via a smooth interface provided between the guide surface 158 of the actuator 150 and the upper surface 60 of the first jaw 32. As best shown in FIG. 6, as the post 130 moves, the second jaw 34 pivots relative to the first jaw 32 at the interface between the mounting members 90 and the engagement segments 138 (one of which is shown in FIG. 6), such that the end section 104 of the second jaw 34 moves laterally away from the end section 64 of the first jaw 32, resulting in an open state of the jaws 32, 34 in which a spacing between the end sections 64, 104 is generated. In the open state, and as shown in FIG. 6, the holding members 78 are spaced from the end section 104 of the second jaw 34, such that the channel 108 is fully open and available to receive an annuloplasty prosthesis (not shown) as described below. Upon removing the user-applied force to the actuator 150 and with reference to FIG. 4C, the biasing device 152 forces the post 130 of the second jaw 34 away from the post 88 of the first jaw 32, thus transitioning the jaws 32, 34 back to a closed state.

Suture Management Device 28

Figure 7A:
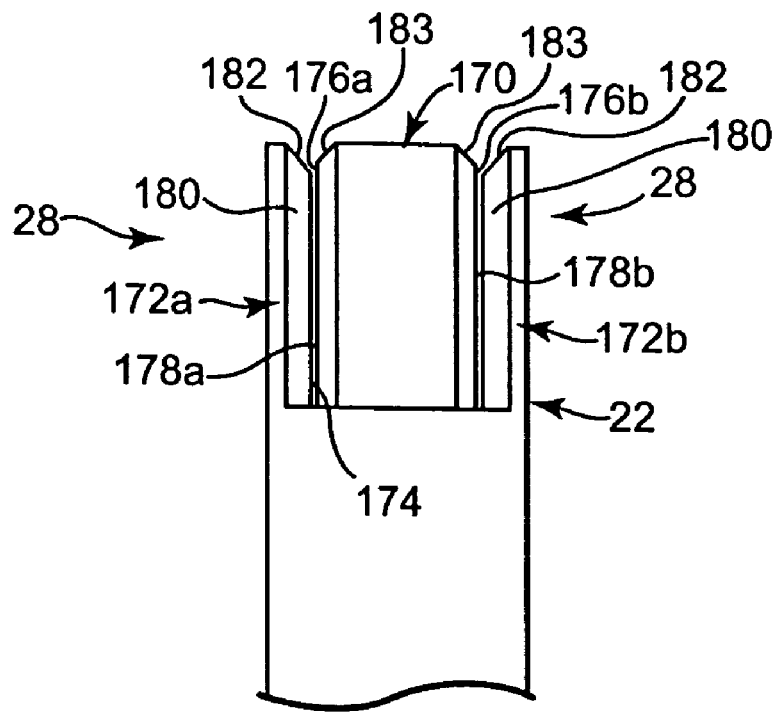
FIG. 7A is an enlarged, top view of a portion of the tool of FIG. 1A illustrating a suture management device in accordance with principles of the present invention.

Returning to FIG. 1B, the suture management device 28 includes, in one embodiment, a flexible, resilient member 170 that is assembled to the proximal portion 22. For example, with reference to FIG. 7A, the proximal portion 22 forms opposing legs 172a, 172b that combine to define a gap 174. The flexible, resilient member 170 is configured to nest within the gap 174 and defines opposing, first and second edges 176a, 176b. To this end, in an undeformed state, the flexible member 170 encompasses a width of the gap 174 (it being understood that for purposes of clarity, the flexible member 170 is shown in FIG. 7 as having a width slightly less than that of the gap 174). Thus, in an undeformed state, the first edge 176a of the flexible member 170 naturally bears against the leg 172a, whereas the second, opposing edge 176b naturally bears against the leg 172b. However, due to the inherent flexible, resilient nature of the flexible member 170, for example by forming the flexible member 170 out of silicone or similar material, the edges 176a, 176b are readily deflected away from the corresponding leg 172a, 172b to form first and second slots 178a, 178b, respectively (it again being understood that in the illustration of FIG. 7A, the slots 178a, 178b are greatly exaggerated in size for purposes of clarity; due to the resilient nature of the flexible member 170, the slots 178a, 178b are not visually perceptible in the natural, undeformed state of the flexible member 170 in accordance with one embodiment). The slots 178a, 178b each provide a receiving zone for selectively maintaining a thin body, such as a suture(s) as described in greater detail below. Each of the slots 178a, 178b are sized and shaped to be capable of holding about ten to twenty 2-0 sutures otherwise used to attach an annuloplasty device to a heart valve annulus.

Figure 7B:
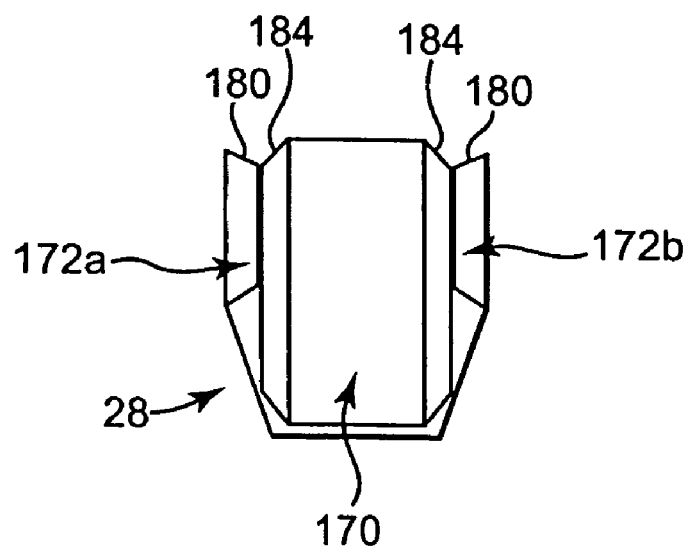
FIG. 7B is an enlarged, simplified end view of the suture management device of FIG. 7A.

To facilitate suture insertion within the slots 178a, 178b, a top surface 180 and a proximal end 182 of each of the legs 172a, 172b are, in one embodiment, formed with a chamfer that guides a suture(s) into the corresponding slot 178a or 178b. This chamfered configuration of the top surface 180 is best shown in FIG. 7B, otherwise illustrating, in simplified form, an end view of the tool 20 (with other components, such as jaws 32, 34 (FIG. 1A) omitted). In another embodiment, and with continued reference to FIGS. 7A and 7B, a proximal edge 183 (FIG. 7A) and an upper surface 184 (FIG. 7B) of the flexible member 170 adjacent the edges 176a, 176b is similarly chamfered. Regardless, the flexible member 170 is adapted to frictionally retain suture(s) against the corresponding leg 172a, 172b, and readily reverts to a configuration in which the flexible member 170 encompasses an entire width of the gap 174 upon removal of the suture(s).

Alternatively, the suture management device 28 can assume a variety of other forms. For example, the flexible member 170 can be formed of a harder material such as hardened plastic. Further, the suture management device 28 can be configured to provide a single-receiving slot or a multiplicity (three or more) of suture-receiving slots. In other embodiments, the suture management device 28 includes one or more clamping mechanisms (e.g., a spring-loaded clamp formed by, or attached to, the proximal end 40 of the handle 30). Along these same lines, in other alternative embodiments, the suture management device 28, or any of the alternative suture management device configurations described above, can be employed with a tool (for use in implanting an annuloplasty prosthesis) that does not include the jaws 32, 34/actuator mechanism 26 described above, but instead incorporates an entirely different prosthesis retaining configuration, such as that associated with conventional annuloplasty device holders (e.g., a body forming a slot within which the prosthesis is received in combination with one or more sutures that secure the prosthesis within the slot).

Methods of Use/Implantation

Figure 8A:
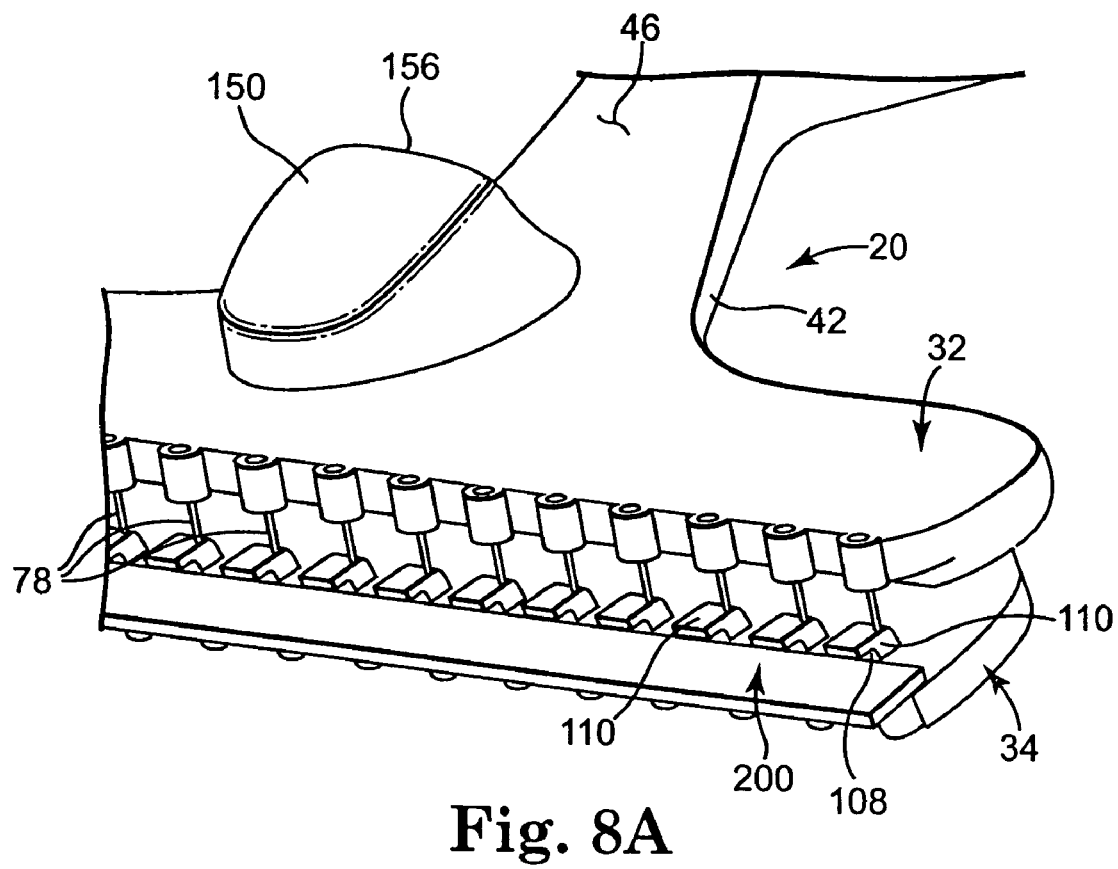
FIG. 8A is a perspective view of the portion of the tool of FIG. 1A with the jaws in an open state in combination with an implantable annuloplasty prosthesis.
Figure 8B:
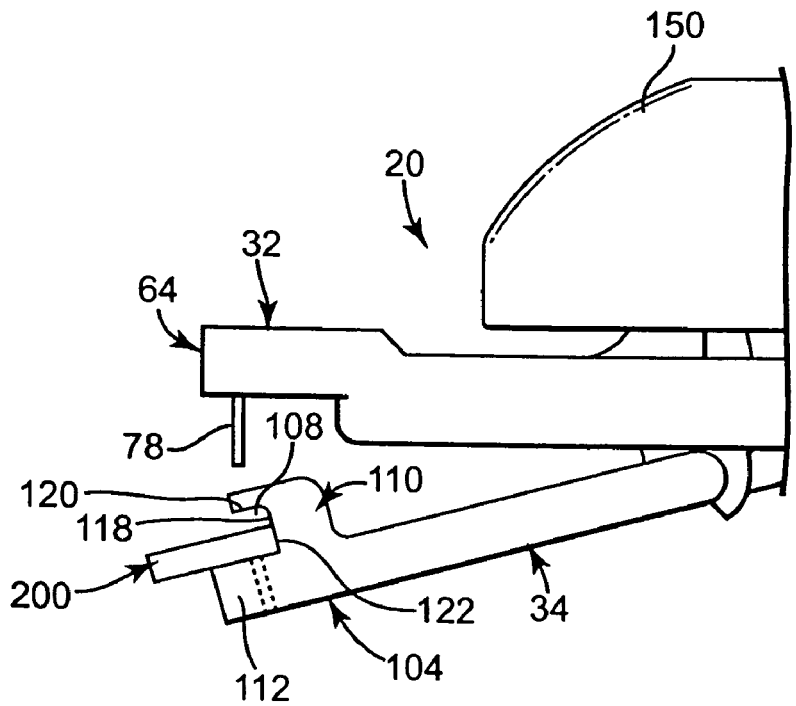
FIG. 8B is a side view of the combination of FIG. 8A.

During use, the tool 20 is capable of holding and releasing an annuloplasty prosthesis in a highly convenient manner to facilitate an implantation procedure. For example, FIGS. 8A and 8B illustrate the distal portion 24 of the tool 20 in combination with an annuloplasty prosthesis 200. The annuloplasty prosthesis 200 is shown generically in FIGS. 8A and 8B, and can assume a variety of forms. For example, in one embodiment, the prosthesis 200 is a flexible annuloplasty band, but alternatively can be an annuloplasty ring. Alternatively, the prosthesis 200 can be any elongated structure, such as a rod, bar, or cord. The prosthesis 200 can be flexible, partially flexible, resilient, or partially resilient. The cross-sectional shape of the prosthesis 200 can be of any suitable shape such as, but not limited to, circular, polygonal, square, rectangular, elliptical, or combinations thereof. The prosthesis 200 can comprise a unitary or composite structure. Alternatively, the prosthesis 200 can be constructed of segments or elements with different properties such as stiffness, rigidity, and/or radiopacity. Optionally, the prosthesis 200 may include a drug or therapeutic agent that tends to be slowly released or eluded from the prosthesis 200.

Regardless of exact configuration, the annuloplasty prosthesis 200 is initially mounted to the tool 20 by first transitioning the jaws 32, 34 to an open state shown in FIG. 8A. In particular, while the handle 30 (FIG. 1A) is grasped by the user's single hand (not shown), the thumb or finger of that hand slides along the upper surface 46 of the neck 42 and easily reaches the actuator button 150, contacting the pressing surface 156 (referenced generally in FIG. 8A). A pushing force is then applied (e.g., by the single digit of the user's hand) to the actuator button 150, causing the actuator mechanism 26 (FIG. 4C) to transition the jaws 32, 34 from a closed state (FIG. 1A) to the open state of FIG. 8A as previously described. With the jaws 32, 34 maintained in the open state (via continuous user-imparted force applied to the actuator button 150), the annuloplasty prosthesis 200 is inserted within the channel 108 (reference generally in FIG. 8A, but shown more clearly in FIG. 6) of the second jaw 34. To this end, insertion of the annuloplasty prosthesis 200 is characterized by the annuloplasty prosthesis 200 contacting the lateral face 118 defined by the fingers 110 and the second longitudinal face 122 provided by the projections 112 as best shown in FIG. 8B. Depending upon a thickness of the annuloplasty prosthesis 200, the first longitudinal face 120 defined by the fingers 110 may also be contacted. Regardless, the second longitudinal face 122 provides a convenient surface for sliding the annuloplasty prosthesis 200 into contact with the lateral face 118, with the lateral face 118 providing a stop surface that ensures a desired position of the annuloplasty prosthesis 200 relative to the holding members 78 (one of which is shown in FIG. 8B).

Figure 9:
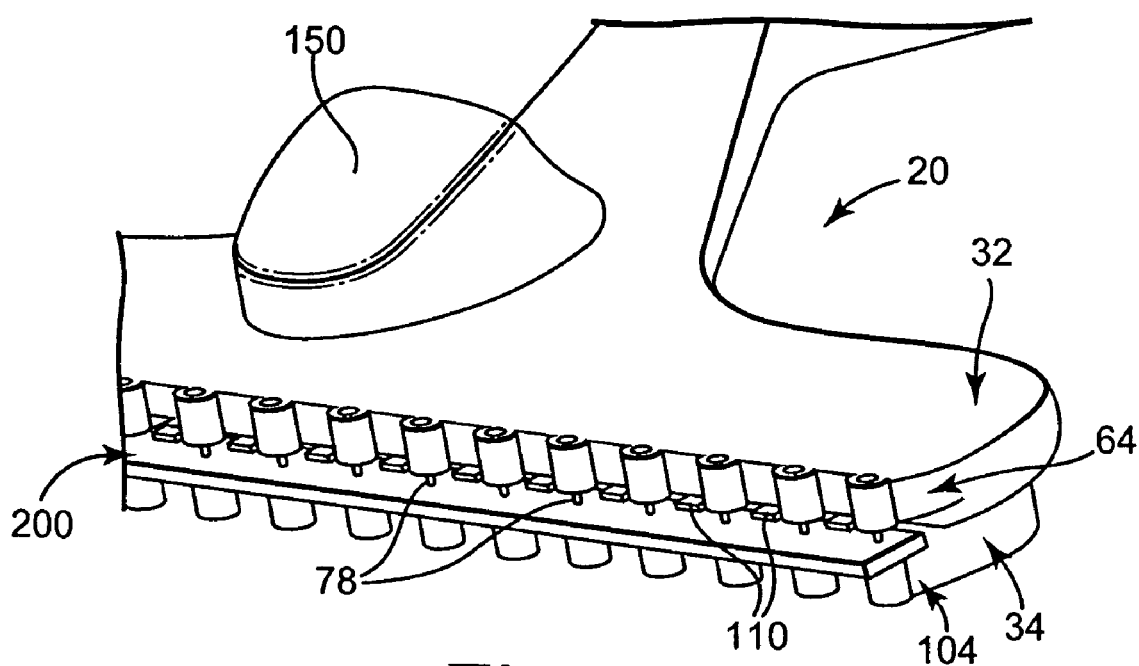
FIG. 9 is an enlarged perspective view of the combination tool/annuloplasty prosthesis, with the jaws in a closed state.

Once inserted, the annuloplasty prosthesis 200 is secured to the tool 20 by transitioning the jaws 32, 34 to a closed state as shown in FIG. 9. More particularly, the user-applied force on the actuator button 150 is removed, with the actuator mechanism 26 (and in particular the biasing device 152 (FIG. 4C)) causing the end section 104 of the second jaw 34 to transition or move toward the end section 64 of the first jaw 32. In the closed state, the holding members 78 pierce or penetrate into the annuloplasty prosthesis 200 (e.g., a cloth covering), thus securing the annuloplasty prosthesis 200 to the tool 20. The biasing device 152 (or other locking-type structure previously described) maintains the jaws 30, 34 in a closed state to prevent dislodgement of the annuloplasty prosthesis 200 from the tool 20. Alternatively, depending upon a configuration of the annuloplasty prosthesis 200 and/or the holding members 78, securement of the annuloplasty device 200 to the tool 20 can take other forms that do not necessarily entail piercing of the annuloplasty device 200. Preferably, however, separate tying device(s) (e.g., sutures) are not required. Regardless, the annuloplasty prosthesis 200 is retained by the tool 20 in a straight line or linear fashion. This allows a surgeon to more clearly identify desired suture spacing along the prosthesis 200 (described below) as opposed to conventional holders that maintain the prosthesis 200 in a curved shape.

The annuloplasty prosthesis 200 can subsequently be released from the tool 20 by transitioning the jaws 32, 34 to an open state (FIG. 8A) as previously described. In this regard, as the end section 104 of the second jaw 34 is transitioned or pivoted away from the end section 64 of the first jaw 32, temporary frictional engagement between the holding members 78 and the annuloplasty prosthesis 200 (e.g., due to piercing of annuloplasty prosthesis 200 by the holding member 20 in one embodiment), may cause the prosthesis 200 to "move" with the first jaw 32. With this in mind, with transition to an open state, the annuloplasty prosthesis 200 contacts or abuts the first longitudinal face 120 (FIG. 8B) of the fingers 110. Thus, the annuloplasty prosthesis 200 remains associated with the second jaw 34, thereby allowing the holding members 78 to fully disengage from the annuloplasty prosthesis 200 as the jaws 32, 34 transition to an open state. Once the holding members 78 have been disengaged, the annuloplasty prosthesis 200 can then easily be removed from the channel 108, and thus the tool 20. Notably, the above-described mounting and removal of the annuloplasty prosthesis 200 is accomplished via single push/point maneuver of the actuator button 150 by a single digit (not shown) of the user's hand (not shown). Unlike previous annuloplasty device holders, the tool 20 of the present invention does not require tying of sutures or similar devices to secure the annuloplasty prosthesis 200 to the tool 20, nor does it require cutting of sutures or any other use of a sharp instrument to effectuate removal of the annuloplasty prosthesis 200 from the tool 20.

With the above understanding of the tool 20/annuloplasty prosthesis 200 relationship in mind, the tool 20 can be used to facilitate a wide verity of heart valve repair procedures, such as, for example, mitral or tricuspid annuloplasty in conjunction with an implantable annuloplasty band or ring.

Figure 10A:
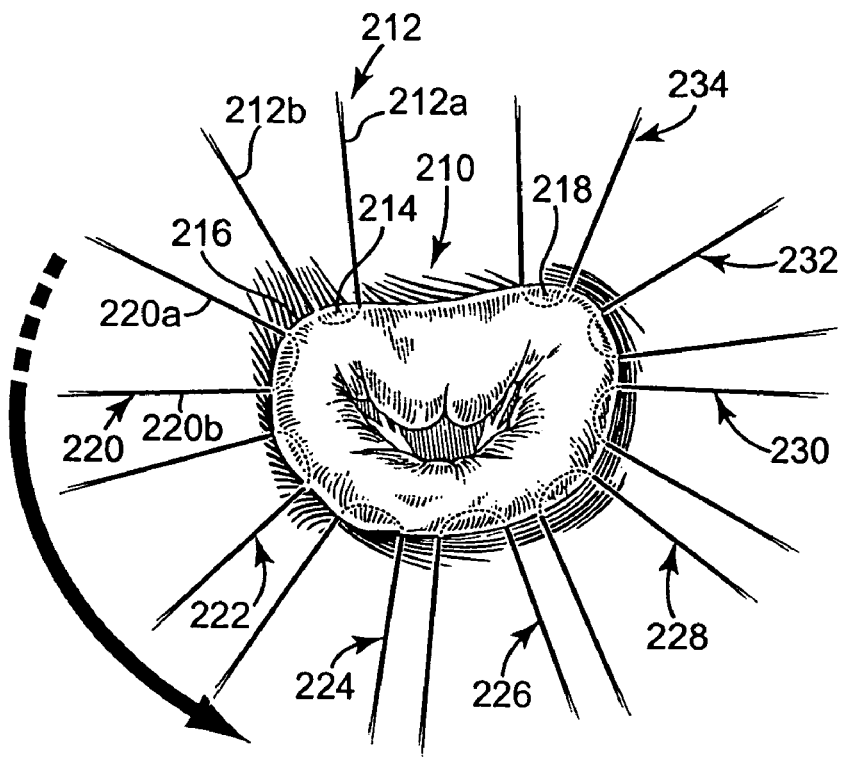
FIGS. 10A-15 illustrate some embodiments of a method for implanting an annuloplasty prosthesis according to principles of the present invention.

Implantation of the annuloplasty prosthesis 200 begins (before or after securing the prosthesis 200 to the tool 20) by placing sutures at the desired target site. For example, FIG. 10A illustrates suture placement relative to a mitral valve annulus 210 in accordance with one embodiment. In particular, a first suture 212 is placed at the left fibrous trigone 214 to define a suture pair (consisting of sutures segments 212a, 212b) approximately 4 mm in width. Working along a posterior 216 of the annulus 210 from the left fibrous trigone 214 to a right fibrous trigone 218 (in a direction indicated by an arrow in FIG. 10A), adjacent interrupted sutures 220-234 are consecutively placed approximately 1-2 mm from the previous suture, with each of the sutures 220-234 forming suture pairs (e.g., the second suture 220 forms a suture pair consisting of segments 220a, 220b, etc.). Each suture/suture pair 220-234 is spaced approximately 4 mm where no plication is necessary, and approximately 5-6 mm in width where plication is desired. The last suture pair 234 (approximately 4 mm in width) is placed at the right fibrous trigone 218. With this one technique, approximately 8-10 sutures may be placed in the mitral valve annulus 210. Alternatively, a variety of other suturing techniques can be employed.

Figure 10B:
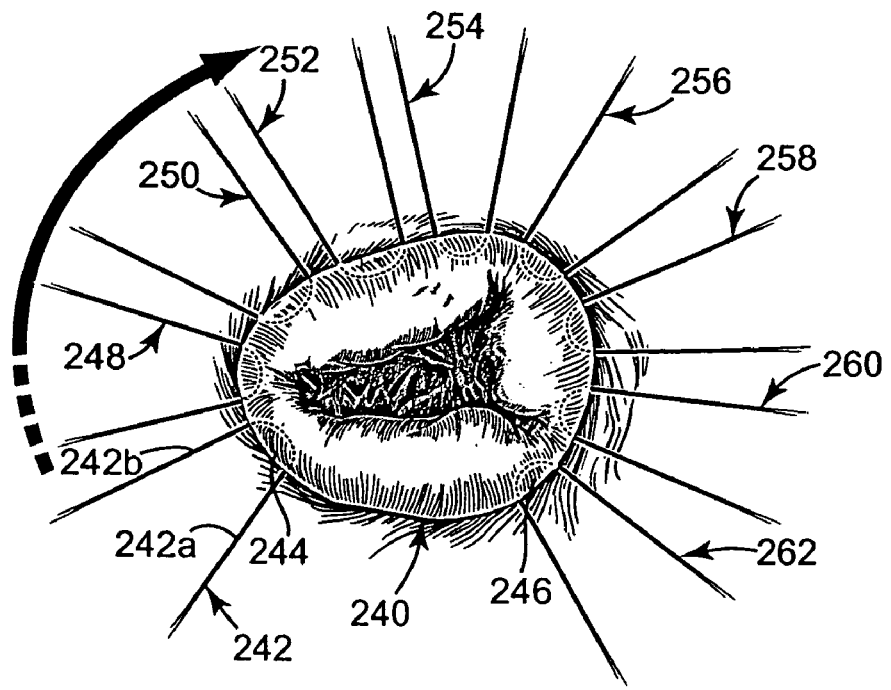

The above-described series-type suture placement can also be employed for repair of a tricuspid valve annulus 240 as shown in FIG. 10B. A first suture 242 is initially placed at a medial fibrous trigone 244 to define a suture pair (i.e., suture segments 242a, 242b). Working along the anterior and posterior annulus 240 from the medial fibrous trigone 244 to a posterior septal commissure 246 (in a direction shown by an arrow in FIG. 10B), adjacent sutures 248-262 (and thus suture pairs) are consecutively placed in an interrupted fashion approximately 1-2 mm from the previous suture pair. Each suture pair 242, 248-262 is spaced approximately 4 mm in width where no plication is necessary, and approximately 5-6 mm in width where plication is desired. The last suture pair 262 is located at the posterior septal commissure 246, and is approximately 4 mm in width. With this technique, approximately 8-12 sutures can be placed in the valve annulus 240. Alternatively, a wide variety of other suturing techniques can be employed.

Figure 11:
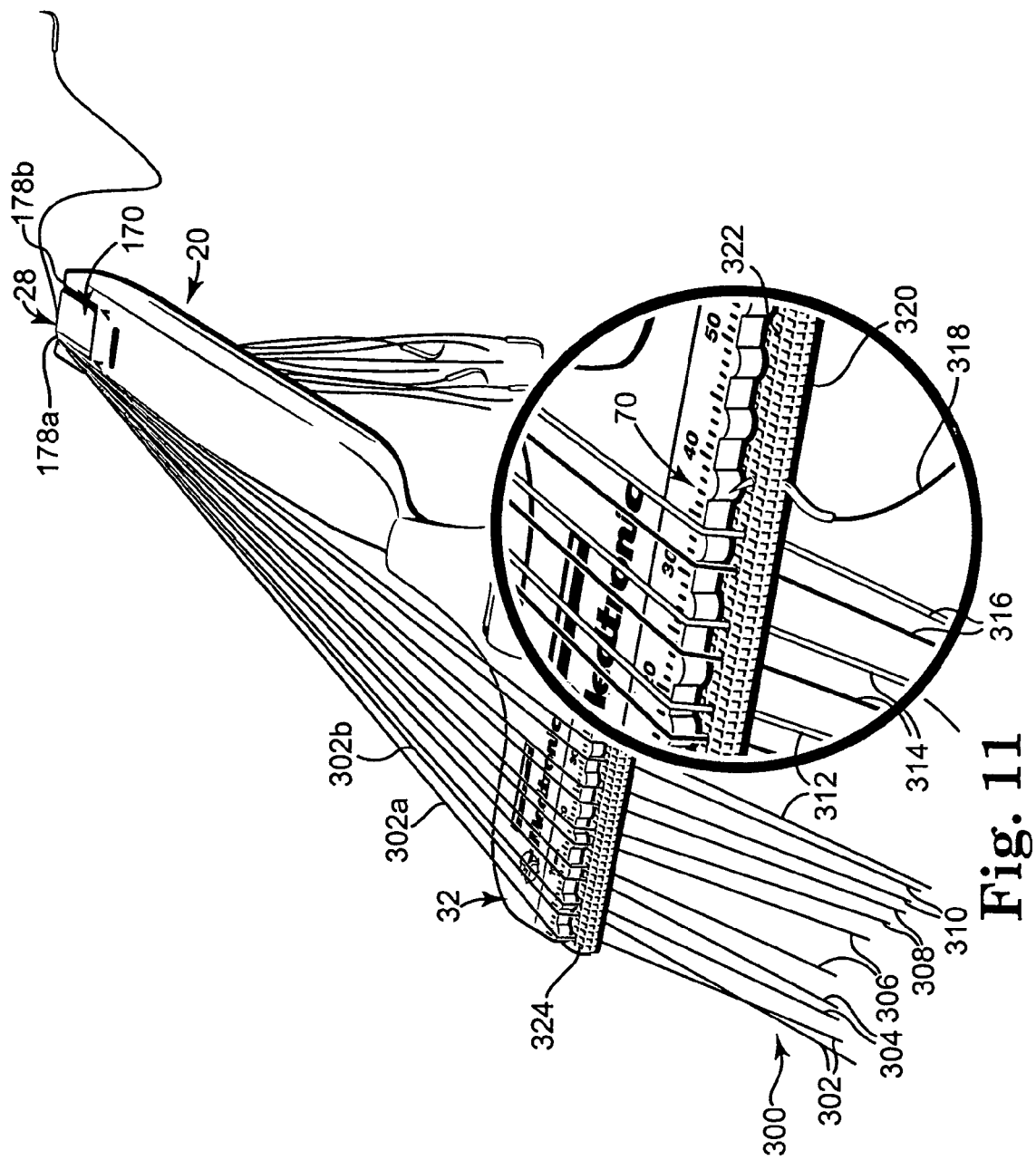

Regardless of the valve being repaired and/or the suture ordering/placement, the sutures are then secured to the annuloplasty prosthesis 200 as shown in FIG. 11. In particular, FIG. 11 illustrates the annuloplasty prosthesis 200 secured to the tool 20, with the jaws 32, 34 in the closed state. In the illustration of FIG. 11, the sutures are generally represented at 300, and consist of a series of suture pairs 302-318 as previously described. All of the sutures 300 are threaded to the annuloplasty prosthesis 200 by, in one embodiment, entering at a bottom 320 of the annuloplasty prosthesis 200 and exiting through a top 322, with each of the sutures 300 being placed at approximately a mid-line of the annuloplasty prosthesis 200. Where provided, the indicia 70 assists in directing the user to a proper location of each of the sutures 300 relative a length of the annuloplasty prosthesis 200. For example, and with reference to the mitral valve annulus 210 of FIG. 10A, the first suture pair 302 (consisting of suture segments 302a, 302b) extends from the left fibrous trigone 214 (FIG. 10A). The first segment 302a is inserted approximately 2 mm from a first end 324 of the annuloplasty prosthesis 200. The indicia 70 preferably includes a marking indicative of this 2 mm location. The second segment 302b is similarly threaded through the annuloplasty prosthesis 200, at a desired spacing relative to the first segment 302a (e.g., on the order of 4-5 mm). Once again, the indicia 70 preferably includes markings indicative of length in 1 mm increments to facilitate desired spacing between the suture segments 302a, 302b relative to the prosthesis 200. Adjacent suture pairs 304-318 are similarly placed through the annuloplasty prosthesis 200 at desired spacings (e.g., adjacent suture pairs are approximately 1-2 mm apart from a previous suture pair).

After placing the individual suture pairs 302-318 through the annuloplasty prosthesis 200, the suture pairs 302-318 can be consecutively organized and secured to the suture management device 28. For example, in one embodiment, after being inserted through the prosthesis 200, each suture segment is inserted within one of the slots 178a, 178b by threading or pressing the suture segment between the edge 176a or 176b (FIG. 7A) of the flexible member 170 and the corresponding leg 172a or 172b (FIG. 7A). The flexible member 170 serves to frictionally retain the sutures within the slot 178a or 178b. Unlike previous techniques, the suture management device 28 is provided as part of the tool 20 in accordance with one embodiment, such that one or more additional, separate components are not required to maintain the sutures 300 in an organized fashion, thereby greatly reducing the time required to perform the procedure. In alternative embodiments, however, separate devices apart from the tool 20 can be employed to maintain the sutures 300.

Figure 12:
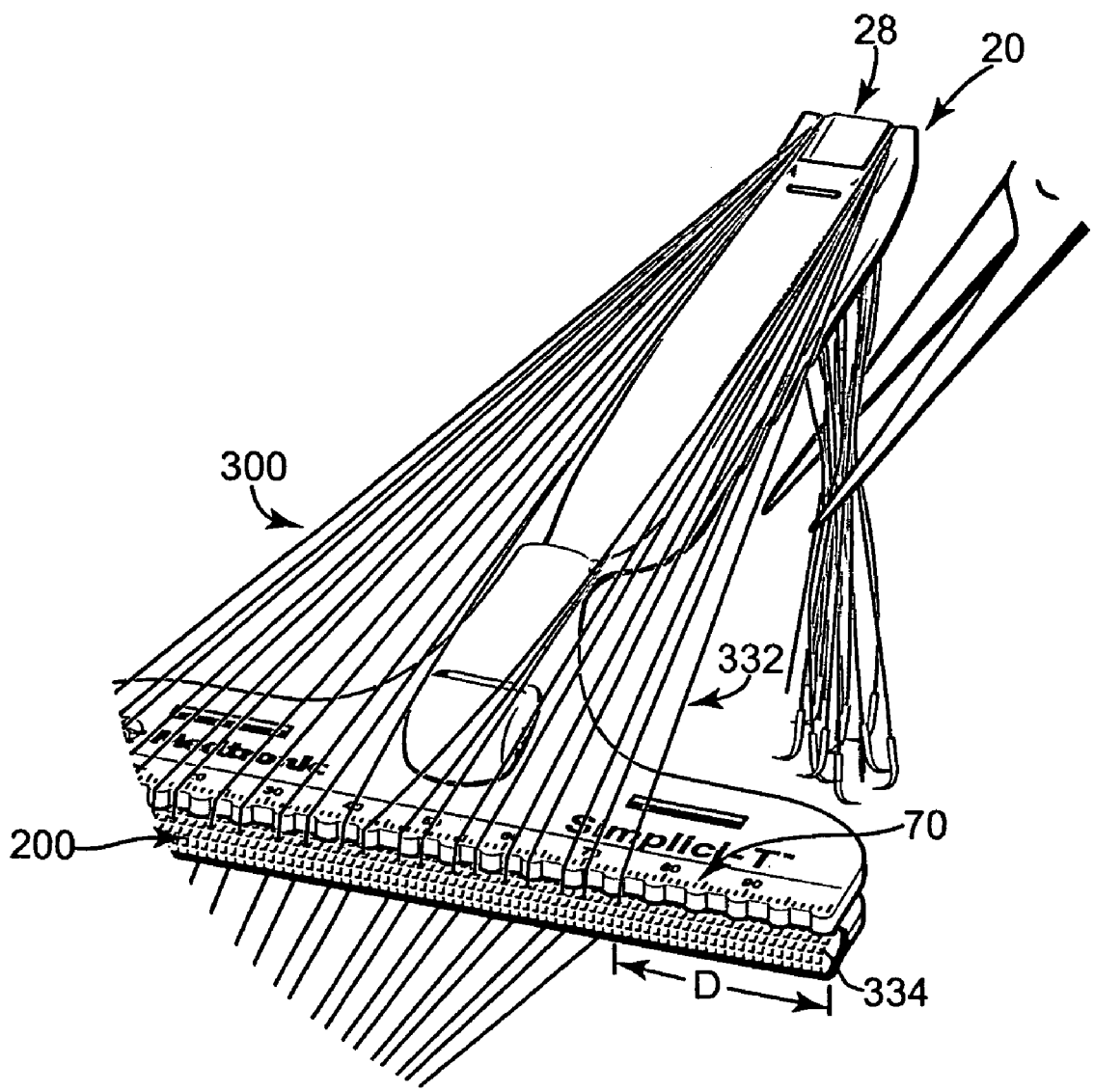

With reference to FIG. 12, once all of the sutures 300 have been secured to the annuloplasty prosthesis 200, the suture needles are removed. The annuloplasty prosthesis 200 can then be removed from the tool 20. Prior to removal, and in accordance with one embodiment, an effective end length of the annuloplasty prosthesis 200 is noted. In particular, and as shown in FIG. 12, a last suture pair 332 has been placed at a relatively significant distance D from a second end 334 of the annuloplasty prosthesis 200. By way of background, and in one embodiment, the annuloplasty prosthesis 200 is initially formed to have an overall length greater than the expected length necessary to accommodate the heart valve annulus being repaired. In other words, the annuloplasty prosthesis 200 is not selected from an inventory of differently-sized devices, but instead is more universally applicable to virtually any sized heart valve annulus. With this in mind, once the last suture pair 332 has been secured to the annuloplasty prosthesis 200, the user will know the final length needed for proper implantation. Thus, in one embodiment, the user records an expected implantation length of the annuloplasty prosthesis 200 by measuring approximately 2 mm past the last suture pair 332. Once again, the indicia 70 facilitate an expedited determination of this implantation length via the graduated markings.

With the implantation length of the annuloplasty prosthesis 200 noted, the suture 300 are removed as a bundle from the suture management device 28. The annuloplasty prosthesis 200 can then be removed from the tool 20 by transitioning the jaws 32, 34 from the closed state of FIG. 12 to an open state of FIG. 13. Once again, transitioning of the jaws 32, 34 to an open state is accomplished by the user (not shown) applying a pushing or sliding force onto the actuator button 150 via the user's thumb or finger. In the open state of FIG. 13, the annuloplasty prosthesis 200 is removed from the channel 108, otherwise provided by the tool 20. Once again, removal of the annuloplasty prosthesis 200 from the tool 20 is characterized by the absence of a need to cut any portion of the tool 20 or otherwise use a sharp instrument.

Figure 13:
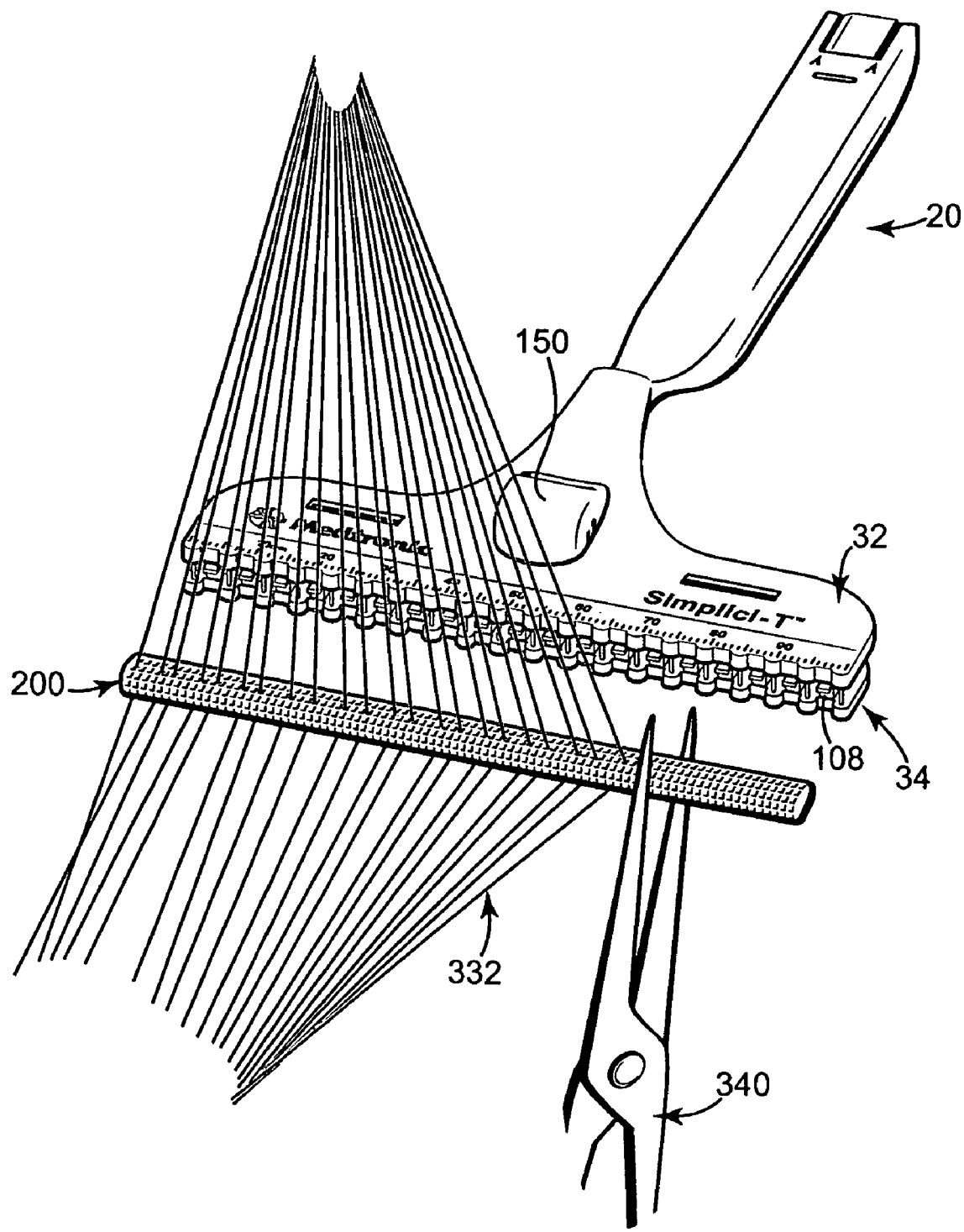

Once the annuloplasty prosthesis 200 has been removed from the tool 20, the tool 20 can be removed from the surgical site. The annuloplasty prosthesis 200 is then cut to define the desired, effective end length. For example, as shown in FIG. 13, a cutting implement 340 can be employed to cut the annuloplasty prosthesis 200 at a point approximately 2 mm from the last suture pair 332. The removed portion of the annuloplasty prosthesis 200 can then be disposed.

Figure 14:
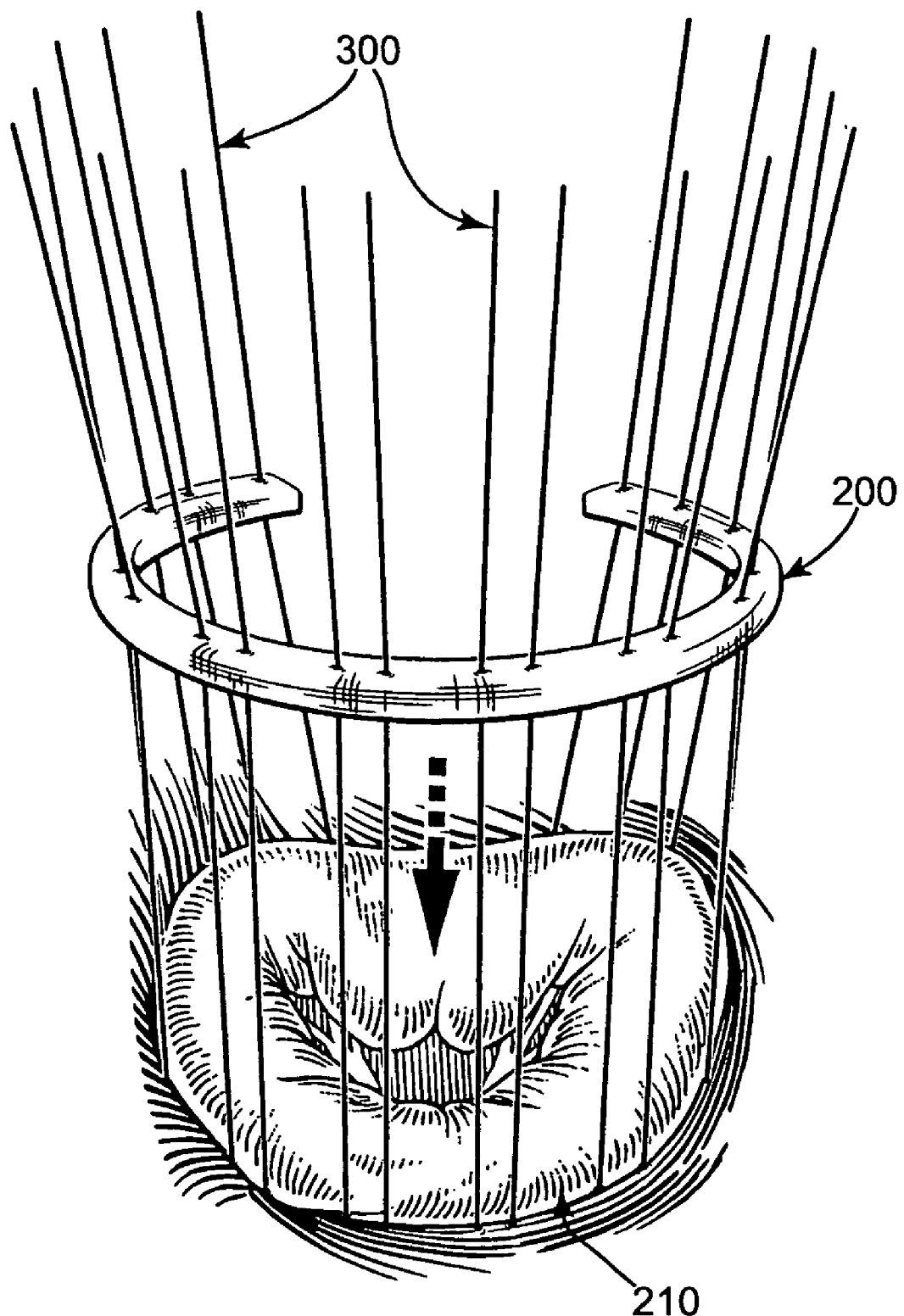

With reference to FIG. 14, the user (not shown) then pushes the appropriately-sized annuloplasty prosthesis 200 along the sutures 300 (e.g., downwardly as shown by an arrow in FIG. 14) onto the valve annulus 210.

Figure 15:
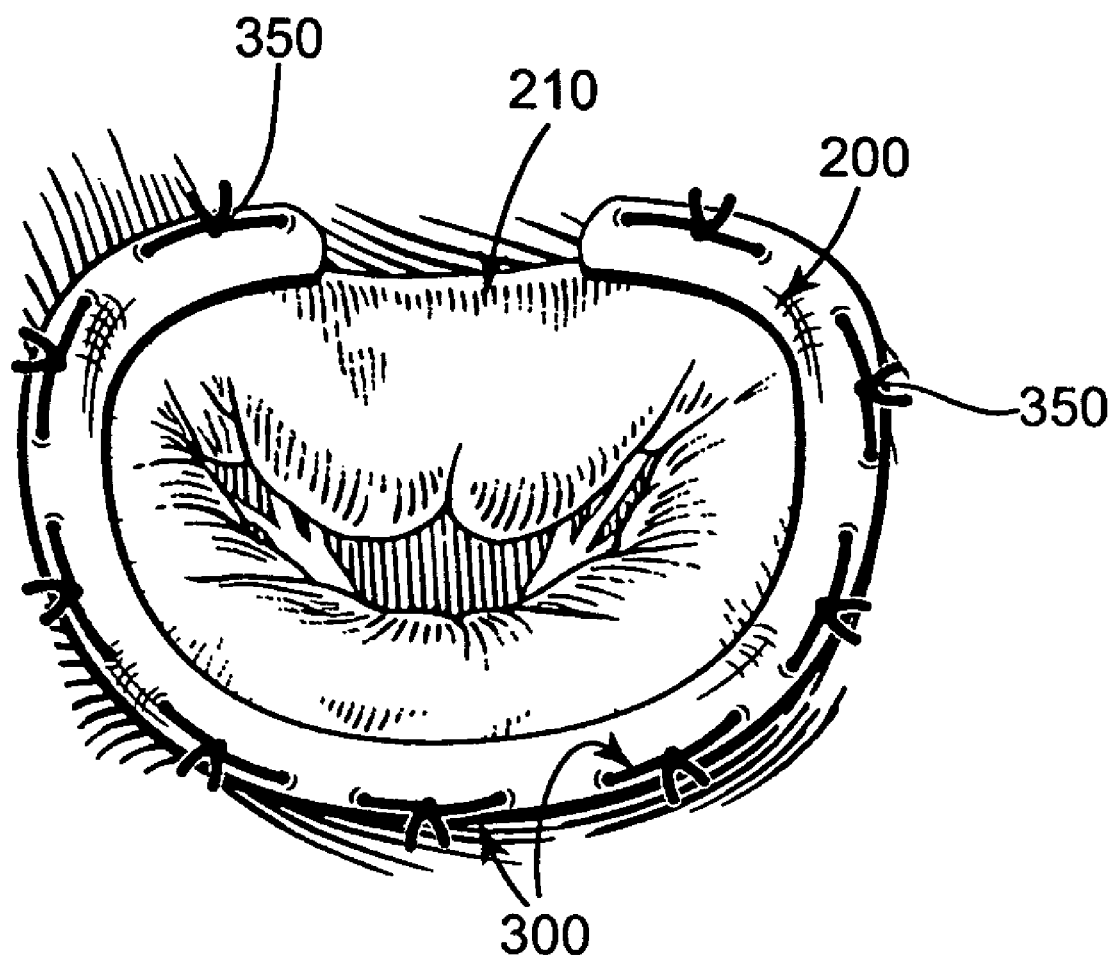

Finally, as shown in FIG. 15, each of the suture pairs 300 are tied via knots 350 to securely hold the annuloplasty prosthesis 200 against the valve annulus 210, and excess suture material is trimmed.

Thus, embodiments of the "Tool and Method for Implanting an Annuloplasty Prosthesis" are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of repairing a heart valve, the method comprising:
   receiving an implantable annuloplasty prosthesis;
   receiving a tool having first and second jaws, at least one of the first and second jaws being movable relative to the other between i) an open state in which an end section of the first jaw is spaced apart from a corresponding end section of the second jaw, and ii) a closed state in which a spacing between the corresponding end sections is less than the spacing in the open state;
   transitioning the jaws to the open state;
   positioning the implantable annuloplasty prosthesis against the end section of at least one of the first and second jaws;
   securing the implantable annuloplasty prosthesis to the tool by transitioning the jaws to the closed state;
   attaching at least one suture to heart tissue;
   passing the suture through the implantable annuloplasty prosthesis while the implantable annuloplasty prosthesis is secured to the tool;
   pressing an actuator of the tool along a surface of one of the jaws toward the end sections to cause transitioning of the jaws to the open state;
   removing the implantable annuloplasty prosthesis from the tool while the jaws are in the open state;
   moving the implantable annuloplasty prosthesis to an implant location;
   securing the at least one suture so that it resists movement of the annuloplasty prosthesis relative to heart tissue;
   wherein transitioning the jaws to the open state includes manipulating a single actuator;
   wherein the tool further includes an actuator mechanism for effectuating transitioning of the jaws from the closed state to the open state, the actuator mechanism including the single actuator and further wherein manipulating the single actuator includes applying a force onto the actuator with a single digit of a user's hand;
   wherein the tool includes a handle, and wherein the method further comprises grasping the handle within a palm of the user's hand and manipulating the handle to position the implantable prosthesis adjecent a target site prior to the step of passing the suture through the prosthesis; and
   wherein the step of pressing the actuator to cause transitioning of the jaws to the open state to facilitate removal of the implantable prosthesis from the tool includes applying a pushing force to the actuator with a thumb of the user's hand while simultaneously maintaining the handle within the palm of the user's hand, the pushing force being applied solely by extending the thumb away from the palm.

2. The method of claim 1, wherein securing the implantable annuloplasty prosthesis to the tool is characterized by the tool maintaining the prosthesis in a linear fashion.

3. The method of claim 1, wherein removing the implantable prosthesis from the tool is characterized by the absence of cutting any portion of the tool.

4. The method of claim 1, wherein passing the suture through the implantable prosthesis further includes:
   securing a segment of the suture to a suture management device provided by the tool.

5. The method of claim 4, wherein the suture management device includes a flexible, resilient member disposed within a gap defined by the handle of the tool, the flexible member and the handle combining to define a slot, and further wherein securing a segment of the suture to the suture management device includes sliding the suture segment within the slot such that the flexible member and the handle frictionally engage the suture.

6. The method of claim 4, further comprising:
   attaching a plurality of sutures to the heart tissue;
   passing each of the plurality of sutures through the implantable prosthesis while the implantable prosthesis is secured to the tool; and
   securing a segment of each of the plurality of sutures to the suture management device.

7. The method of claim 6, wherein the suture management device includes a flexible, resilient member disposed within a gap defined by two legs at a proximal end of the handle of the tool, the flexible member and the legs combining to define first and second slots, and further wherein securing the plurality of sutures to the suture management device includes securing at least one suture in the first slot and a second suture in the second slot.

8. The method of claim 6, further comprising:
organizing the plurality of sutures in the suture management device.

9. The method of claim 1, wherein transitioning the jaws to the closed state includes removing the thumb-applied pushing force from the actuator, the actuator mechanism adapted to self-effect transitioning to the closed state upon removal of the pushing force.

10. The method of claim 1, wherein the step of positioning the implantable annuloplasty prosthesis against the end section of at least one of the first and second jaws includes supporting the implantable annuloplasty prosthesis along two planes by the end section of the first jaw.

11. The method of claim 1, wherein the first jaw includes a lower surface facing the second jaw and an upper surface opposite the lower surface, and further wherein the step of pressing the single actuator includes sliding the single actuator along the upper surface.

12. A method of repairing a heart valve, the method comprising:
receiving an implantable annuloplasty prosthesis;
receiving a tool having first and second jaws, at least one of the first and second jaws being movable relative to the other between i) an open state in which an end section of the first jaw is spaced apart from a corresponding end section of the second jaw, and ii) a closed state in which a spacing between the corresponding end sections is less than the spacing in the open state;
transitioning the jaws to the open state;
positioning the implantable annuloplasty prosthesis against the end section of at least one of the first and second jaws;
securing the implantable annuloplasty prosthesis to the tool by transitioning the jaws to the closed state;
attaching at least one suture to heart tissue;
passing the suture through the implantable annuloplasty prosthesis while the implantable annuloplasty prosthesis is secured to the tool;
wherein transitioning the jaws to the open state includes manipulating a single actuator;
wherein the tool further includes an actuator mechanism for effectuating transitioning of the jaws from the closed state to the open state, the actuator mechanism including the single actuator and further wherein manipulating the single actuator includes applying a force onto the actuator with a single digit of a user's hand;
grasping a handle of the tool within a palm of the user's hand and manipulating the handle to position the implantable prosthesis adjacent a target site prior to the step of passing the suture through the prosthesis;
pressing the single actuator of the tool toward the end sections to cause transitioning of the jaws to the open state, wherein the step of pressing the single actuator to cause transitioning of the jaws to the open state to facilitate removal of the implantable prosthesis from the tool includes applying a pushing force to the single actuator with a thumb of the user's hand while simultaneously maintaining the handle within the palm of the user's hand, the pushing force being applied solely by extending the thumb away from the palm, wherein transitioning the jaws to the closed state includes removing the thumb-applied pushing force from the single actuator, the actuator mechanism adapted to self-effect transitioning to the closed state upon removal of the pushing force;
removing the implantable annuloplasty prosthesis from the tool while the jaws are in the open state;
moving the implantable annuloplasty prosthesis to an implant location; and
securing the at least one suture so that it resists movement of the annuloplasty prosthesis relative to heart tissue.

13. A method of repairing a heart valve, the method comprising:
receiving an implantable annuloplasty prosthesis;
receiving a tool having first and second jaws, at least one of the first and second jaws being movable relative to the other between i) an open state in which an end section of the first jaw is spaced apart from a corresponding end section of the second jaw, and ii) a closed state in which a spacing between the corresponding end sections is less than the spacing in the open state;
transitioning the jaws to the open state;
positioning the implantable annuloplasty prosthesis against the end section of at least one of the first and second jaws;
securing the implantable annuloplasty prosthesis to the tool by transitioning the jaws to the closed state;
attaching at least one suture to heart tissue;
passing the suture through the implantable annuloplasty prosthesis while the implantable annuloplasty prosthesis is secured to the tool;
pressing an actuator of the tool toward the end sections to cause transitioning of the jaws to the open state, wherein the first jaw includes a lower surface facing the second jaw and an upper surface opposite the lower surface, and further wherein the step of pressing the actuator includes sliding the actuator along the upper surface;
removing the implantable annuloplasty prosthesis from the tool while the jaws are in the open state;
moving the implantable annuloplasty prosthesis to an implant location; and
securing the at least one suture so that it resists movement of the annuloplasty prosthesis relative to heart tissue.

* * * * *